(12) United States Patent
Whittaker et al.

(10) Patent No.: US 9,977,013 B2
(45) Date of Patent: May 22, 2018

(54) ASSAYS FOR B-TYPE NATRIURETIC PEPTIDE ANALOGUES RESISTANT TO PROLYL-SPECIFIC DIPEPTIDYL DEGRADATION

(71) Applicant: ALERE SAN DIEGO, INC., San Diego, CA (US)

(72) Inventors: Michael A. Whittaker, San Diego, CA (US); Kenneth F. Buechler, San Diego, CA (US)

(73) Assignee: ALERE SAN DIEGO, INC., San Diego, CA (US)

( * ) Notice: Subject to any disclaimer, the term of this patent is extended or adjusted under 35 U.S.C. 154(b) by 0 days. days.

(21) Appl. No.: 15/293,262

(22) Filed: Oct. 13, 2016

(65) Prior Publication Data

US 2017/0138932 A1    May 18, 2017

Related U.S. Application Data

(63) Continuation-in-part of application No. 14/547,801, filed on Nov. 19, 2014, now abandoned, which is a continuation of application No. 12/391,157, filed on Feb. 23, 2009, now abandoned, which is a continuation of application No. 11/560,425, filed on Nov. 16, 2006, now abandoned, and a continuation-in-part of application No. 10/645,874, filed on Aug. 20, 2003, now abandoned.

(51) Int. Cl.
*G01N 33/53* (2006.01)
*G01N 33/68* (2006.01)
*G01N 33/74* (2006.01)
*G01N 33/543* (2006.01)

(52) U.S. Cl.
CPC ....... *G01N 33/5306* (2013.01); *G01N 33/543* (2013.01); *G01N 33/68* (2013.01); *G01N 33/6827* (2013.01); *G01N 33/74* (2013.01); *G01N 2400/02* (2013.01); *G01N 2440/38* (2013.01)

(58) Field of Classification Search
CPC .... G01N 33/53; G01N 33/5306; G01N 33/68; G01N 33/6803; G01N 33/6827; G01N 33/74; G01N 2400/02; G01N 2440/38
See application file for complete search history.

(56) References Cited

U.S. PATENT DOCUMENTS

| | | | |
|---|---|---|---|
| 2004/0176914 A1* | 9/2004 | Buechler | C07K 16/005 702/19 |
| 2005/0148024 A1* | 7/2005 | Buechler | A61K 38/05 435/7.1 |
| 2008/0221033 A1* | 9/2008 | Seher | G01N 33/74 514/1.1 |

OTHER PUBLICATIONS

Clerico et al. State of the art of immunoassay methods for B-type natriuretic peptides: An update. Critical Reviews in Clinical Laboratory Sciences. 2015, vol. 52, No. 2, pp. 56-69.*
Nikishimi et al. Direct Immunochemiluminescent Assay for proBNP and Total BNP in Human Plasma . . . PLoS One 8(1):e53233 (2013).*

* cited by examiner

*Primary Examiner* — Jeffrey E. Russel
(74) *Attorney, Agent, or Firm* — Steptoe & Johnson LLP

(57) ABSTRACT

Methods for improving immunoassays, and in particular, assays for B-Type natriuretic peptide analogues resistant to prolyl-specific dipeptidyl degradation are provided wherein one or more antibodies are selected such that the one or more antibodies detect a biologically active form of a natriuretic peptide of interest.

11 Claims, 1 Drawing Sheet

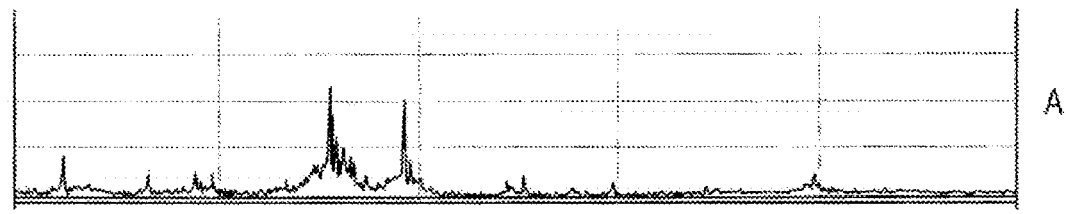
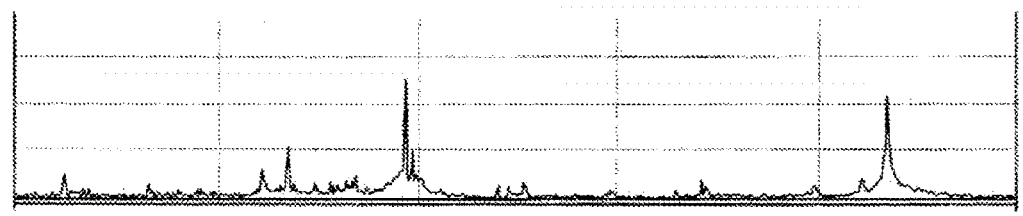
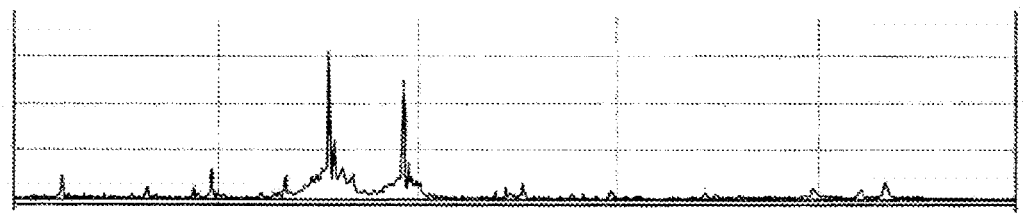
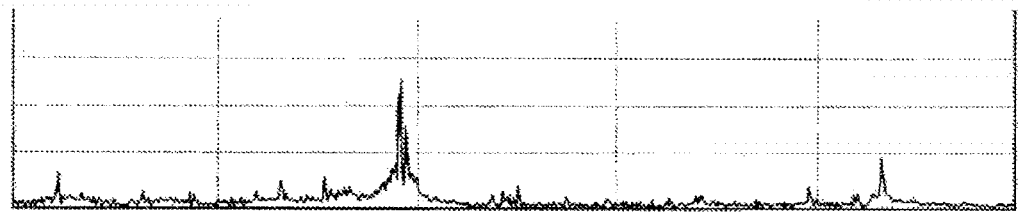
3000   4000   5000
Daltons

SEQUENCE LISTING

```
<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95
```

Ser Ser Gly Leu Gly Cys Lys Val Leu Arg Arg His
            100                 105

<210> SEQ ID NO 2
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 3
<211> LENGTH: 126
<212> TYPE: PRT
<213> ORGANISM: Homo sapiens

<400> SEQUENCE: 3

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Asp Pro Asn Glu Glu Ala Gly Ala Ala
        35                  40                  45

Leu Ser Pro Leu Pro Glu Val Pro Pro Trp Thr Gly Glu Val Ser Pro
50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr
        115                 120                 125

<210> SEQ ID NO 4
<211> LENGTH: 151
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Met Ser Ser Phe Ser Thr Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
        50                  55                  60

Asp Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150

<210> SEQ ID NO 5
<211> LENGTH: 126
<212> TYPE: PRT
<213> ORGANISM: Homo sapiens

<400> SEQUENCE: 5

Met His Leu Ser Gln Leu Leu Ala Cys Ala Leu Leu Leu Thr Leu Leu
1               5                   10                  15

Ser Leu Arg Pro Ser Glu Ala Lys Pro Gly Ala Pro Pro Lys Val Pro
            20                  25                  30

Arg Thr Pro Pro Ala Glu Glu Leu Ala Glu Pro Gln Ala Ala Gly Gly
            35                  40                  45

Gly Gln Lys Lys Gly Asp Lys Ala Pro Gly Gly Gly Ala Asn Leu
        50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu Gln Glu His Pro Asn Ala Arg
                85                  90                  95

Lys Tyr Lys Gly Ala Asn Lys Lys Gly Leu Ser Lys Gly Cys Phe Gly
            100                 105                 110

Leu Lys Leu Asp Arg Ile Gly Ser Met Ser Gly Leu Gly Cys
        115                 120                 125

ASSAYS FOR B-TYPE NATRIURETIC PEPTIDE ANALOGUES RESISTANT TO PROLYL-SPECIFIC DIPEPTIDYL DEGRADATION

CROSS-REFERENCE

This application is a continuation-in-part of U.S. patent application Ser. No. 14/547,801 filed on Nov. 19, 2014, which is a continuation of U.S. patent application Ser. No. 12/391,157, filed on Feb. 23, 2009, which is a continuation of U.S. patent application Ser. No. 11/560 425 filed Nov. 16, 2006, which is a continuation-in-part of U.S. patent application Ser. No. 10/645,874, filed Aug. 20, 2003 each to which this application claims priority, and each of which is hereby incorporated by reference in its entirety, including all tables, figures, and claims.

SEQUENCE LISTING

The instant application contains a Sequence Listing which has been submitted in ASCII format via EFS-Web and is hereby incorporated by reference in its entirety. Said ASCII copy, created on Nov. 19, 2014 is named 36671-744-303-Seqlist.txt and is 7 Kilobytes in size.

FIELD OF THE INVENTION

The present invention relates to medical diagnostics and therapeutics.

BACKGROUND OF THE INVENTION

The following discussion of the background of the invention is merely provided to aid the reader in understanding the invention and is not admitted to describe or constitute prior art to the present invention.

Natriuretic peptides are a group of naturally occurring substances that act in the body to oppose the activity of the renin-angiotensin system. There are three major natriuretic peptides: atrial natriuretic peptide (ANP), which is synthesized in the atria; brain-type natriuretic peptide (BNP), which is synthesized in the ventricles; and C-type natriuretic peptide (CNP), which is synthesized in the brain.

Mature human A-type natriuretic peptide (ANP) (also referred to as atrial natriuretic peptide) is a biologically active 28 amino acid peptide that is synthesized, stored, and released by atrial myocytes in response to atrial distension, angiotensin II stimulation, endothelin, and sympathetic stimulation (beta-adrenoceptor mediated). Mature ANP is generated by proteolytic cleavage of a 128 amino acid precursor molecule (pro-ANP), yielding the biologically active 28 amino acid peptide representing amino acids 99-126 of the pro-ANP molecule ($ANP_{99-126}$). Linear peptide fragments from the N-terminal prohormone segment have also been reported to have biological activity.

Mature human B-type natriuretic peptide (BNP) (also called brain-type natriuretic peptide) is a 32 amino acid, 4 kDa biologically active peptide that is involved in the natriuresis system to regulate blood pressure and fluid balance (Bonow, R. O., *Circulation* 93:1946-1950, 1996). The mature BNP hormone is generated by proteolytic cleavage of a 108-amino acid precursor molecule, referred to herein as "pro-BNP." Cleavage generates t a 76-amino acid N-terminal peptide (amino acids 1-76), referred to as "NT pro BNP," and the 32-amino acid mature hormone, referred to as BNP or BNP 32 (amino acids 77-108). It has been suggested that each of these species—NT pro-BNP, BNP-32, and the pre-pro-BNP—can circulate in human plasma (Tateyama et al., *Biochem. Biophys. Res. Commun.* 185:760-7, 1992; Hunt et al., *Biochem. Biophys. Res. Commun.* 214:1175-83, 1995).

Mature human C-type natriuretic peptide (CNP) a 22-amino acid peptide that is the primary active natriuretic peptide in the human brain; CNP is also considered to be an endothelium-derived relaxant factor, which acts in the same way as nitric oxide (NO) (Davidson et al., *Circulation* 93:1155-9, 1996). CNP is structurally related to A-type natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., *Biochem. Biophys. Res. Commun.* 286:513-7, 2001). CNP is thought to possess vasodilator effects on both arteries and veins and has been reported to act mainly on the vein by increasing the intracellular cGMP concentration in vascular smooth muscle cells.

ANP and BNP are released in response to atrial and ventricular stretch, respectively, and will cause vasorelaxation, inhibition of aldosterone secretion in the adrenal cortex, and inhibition of renin secretion in the kidney. Both ANP and BNP will cause natriuresis and a reduction in intravascular volume, effects amplified by the antagonism of antidiuretic hormone (ADH). The physiologic effects of CNP differ from those of ANP and BNP; CNP has a hypotensive effect, but no significant diuretic or natriuretic actions. Increased blood levels of natriuretic peptides have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; and WO 03/016910, each of which is hereby incorporated in its entirety, including all tables, figures, and claims. Numerous non-human homologs of the natriuretic peptides are known to those of skill in the art.

The natriuretic peptides, alone, collectively, and/or together with additional proteins, can serve as disease markers and indicators of prognosis in various cardiovascular conditions. For example, BNP, which is synthesized in the cardiac ventricles and correlates with left ventricular pressure, amount of dyspnea, and the state of neurohormonal modulation, makes this peptide the first potential marker for heart failure. Measurement of plasma BNP concentration is evolving as a very efficient and cost effective mass screening technique for identifying patients with various cardiac abnormalities regardless of etiology and degree of LV systolic dysfunction that can potentially develop into obvious heart failure and carry a high risk of a cardiovascular event. Finding a simple blood test that would aid in the diagnosis and management of patients with CHF clearly would have a favorable impact on the staggering costs associated with the disease.

Removal of the natriuretic peptides from the circulation is affected mainly by binding to clearance receptors and enzymatic degradation in the circulation. See, e.g., Cho et al., *Heart Dis.* 1: 305-28, 1999; Smith et al., *J. Endocrinol.* 167: 239-46, 2000. Additionally, human pro-BNP is reported to be processed in serum such that circulating pre-pro-BNP is unlikely to be the intact 108 amino acid form. Hunt et al., *Peptides* 18: 1475-81, 1997. Degradation of the natriuretic peptides is believed mediated by neutral endopeptidase. For example, Norman et al. (*Biochem. Biophys. Res. Commun.* 28: 175: 22-30, 1991) report that neutral endopeptidase can cleave human BNP between residues 2 and 3, between residues 4 and 5, and between residues 17 and 18. Similarly, Lindberg and Andersson (*Regul. Pept.* 47: 53-63, 1993) report that human ANP is cleaved between residues 3 and 4 and residues 14 and 15. The biological activity of this hydrolyzed product was about 500-fold less than intact ANP. Additionally, Knecht et al. (*Life Sci.* 71: 2701-12, 2002) report that renal neutral endopeptidase is upregulated in heart failure, a condition where natriuretic peptide levels are increased. For this reason, neutral endopeptidase has been targeted for inhibition in treatment of cardiovascular disease. See, e.g., Corti et al., *Circulation* 104: 1856-62, 2001.

Confusion over the stability of the natriuretic peptides, particularly in blood-derived samples (e.g., serum, plasma, whole blood) has been reported. ANP is reported to be a better substrate for neutral endopeptidase than is BNP. Similarly, Shimizu et al. (*Clin. Chem. Acta* 305: 181-6, 2001), Gobinet-Georges et al. (*Clin. Chem. Lab. Med.* 38: 519-23, 2000) and Murdoch et al. (*Heart* 78: 594-7, 1997) report that BNP is stable in certain blood-derived samples or when blood is collected under certain conditions. A more recent report by Shimizu et al. (*Clin. Chem. Acta* 316: 129-35, 2002) indicates that 94% of BNP in whole blood was a digested form in which 2 amino terminal residues had been removed; and that BNP in plasma was degraded to a number of unidentified forms.

SUMMARY OF THE INVENTION

The present invention relates in part to compositions and methods designed to determine the presence or amount of biologically active natriuretic peptides, or their fragments, in a sample. The degradation of natriuretic peptides is an ongoing process that may be a function of, inter alia, the elapsed time between onset of an event triggering natriuretic peptide release into the tissues and the time the sample is obtained or analyzed; the quantity of proteolytic enzymes present; etc. This degradation can produce circulating amounts of natriuretic peptides having reduced or lost biological function (referred to herein for convenience as "inactive fragments" of a natriuretic peptide).

Failure to consider this degradation when designing an assay for one or more natriuretic peptides may result in an assay that detects both biologically active forms of a natriuretic peptide(s) of interest, as well as inactive fragments of the natriuretic peptide(s). This may lead to the conclusion that an assay shows particularly good stability (i.e., the analyte of interest is not lost to the assay during sample storage), when in fact the natriuretic peptide of interest is actually being degraded to an inactive fragment and the assay result is confounded by the inability to distinguish the intended analyte from the pool of inactive fragments originally present in the sample. Because the biologically active forms may be more relevant to the physiologic state of the subject, and because upregulated proteolytic enzymes in diseased subjects may lead to particularly large pools of inactive fragments in the subjects of potentially the greatest interest, the compositions and methods described herein may provide improved diagnostic and prognostic information to the artisan in comparison to assays that are not specific for the biologically active forms.

The methods and compositions described herein can meet the need in the art for rapid, sensitive and specific diagnostic assay to be used in the diagnosis and differentiation of various cardiovascular diseases, including stroke, congestive heart failure (CHF), cardiac ischemia, systemic hypertension, and/or acute myocardial infarction. Moreover, the methods and compositions of the present invention can also be used to facilitate the treatment of patients and the development of additional diagnostic and/or prognostic indicators and indicator panels.

An improved immunoassay method for determining the presence or amount of a biologically active natriuretic peptide of interest includes contacting a sample with a first antibody selected to bind biologically active forms of the natriuretic peptide of interest, contacting the sample with a second antibody selected to bind all biologically active and biologically inactive forms of the natriuretic peptide of interest, contacting the sample with a third antibody selected to bind the biologically active and biologically inactive forms of the natriuretic peptide when complexed with the first or second antibodies respectively, and determining a first assay signal due to the first antibody and a second assay signal due to the second antibody present in complex with the third antibody, wherein the first assay signal represents the amount of biologically active natriuretic peptide of interest and the second signal represents the total amount natriuretic peptide of interest in the sample.

In certain embodiments, one or more antibodies are selected such that in the immunoassay the one or more antibodies bind to one or more regions of the natriuretic peptides of interest that are not subject to interference by glycosylation.

In a first aspect then, the present invention relates to methods for detecting the presence or amount of a natriuretic peptide in a sample, comprising performing an assay that detects a biologically active natriuretic peptide, but that exhibits at least a 5-fold reduction in signal from, and preferably does not appreciably detect, one or more biologically inactive fragments of the natriuretic peptide. Biologically inactive fragments may include those in which residues from either or both of the N-terminus or C-terminus of the biologically active natriuretic peptide have been removed, and/or in which the loop formed by intramolecular disulfide bonding of the natriuretic peptide has been cleaved. Such biologically inactive fragments may be formed, for example, by cleaving one or more peptide bonds in the biologically active natriuretic peptide.

In related aspects, the present invention relates to methods for detecting the presence or amount of a natriuretic peptide in a sample, comprising performing an assay that detects an intact natriuretic peptide, but that exhibits at least a 5-fold reduction in signal from, and preferably does not appreciably detect, an equimolar amount of a peptide that is generated when a portion, and preferably at least an N-terminal portion, of the intact natriuretic peptide is removed.

In various embodiments, the present invention relates to methods for detecting the presence or amount of BNP in a sample, comprising performing an assay that detects $BNP_{77-108}$, but that exhibits at least a 5-fold reduction in signal from, and preferably does not appreciably detect, an equimolar amount of $BNP_{94-108}$; the assay detects $BNP_{77-108}$, but exhibits at least a 5-fold reduction in signal from, and preferably does not appreciably detect, $BNP_{90-108}$; the assay detects $BNP_{77-108}$, but exhibits at least a 5-fold reduction in signal from, and preferably does not appreciably detect, $BNP_{81-108}$; the assay detects $BNP_{77-108}$, but exhibits at least a 5-fold reduction in signal from, and preferably does not appreciably detect, $BNP_{79-108}$; the assay detects $BNP_{77-108}$, but exhibits at least a 5-fold reduction in signal from, and preferably does not appreciably detect, $BNP_{77-106}$; and/or the assay detects $BNP_{77-108}$, but exhibits at least a 5-fold reduction in signal from, and preferably does not appreciably detect, $BNP_{79-106}$.

In various additional embodiments, the present invention relates to methods for detecting the presence or amount of BNP in a sample, comprising performing an assay that detects $BNP_{1-76}$, but that exhibits at least a 5-fold reduction in signal from, and preferably does not appreciably detect, an equimolar amount of $BNP_{38-76}$; the assay detects $BNP_{1-76}$, but exhibits at least a 5-fold reduction in signal from, and preferably does not appreciably detect, $BNP_{24-76}$; the assay detects $BNP_{1-76}$, but exhibits at least a 5-fold reduction in signal from, and preferably does not appreciably detect, $BNP_{12-76}$; the assay detects $BNP_{1-76}$, but exhibits at least a 5-fold reduction in signal from, and preferably does not appreciably detect, $BNP_{3-76}$; the assay detects $BNP_{1-76}$, but exhibits at least a 5-fold reduction in signal from, and preferably does not appreciably detect, $BNP_{1-73}$; and/or the assay detects $BNP_{1-76}$, but exhibits at least a 5-fold reduction in signal from, and preferably does not appreciably detect, $BNP_{3-73}$.

In still other additional embodiments, the present invention relates to methods for detecting the presence or amount of ANP in a sample, comprising performing an assay that detects $ANP_{99-126}$, but that exhibits at least a 5-fold reduction in signal from, and preferably does not appreciably detect, an equimolar amount of $ANP_{113-126}$; the assay detects $ANP_{99-126}$, but exhibits at least a 5-fold reduction in signal from, and preferably does not appreciably detect, $ANP_{105-126}$; the assay detects $ANP_{99-126}$, but exhibits at least a 5-fold reduction in signal from, and preferably does not appreciably detect, $ANP_{102-126}$, the assay detects $ANP_{99-126}$, but exhibits at least a 5-fold reduction in signal from, and preferably does not appreciably detect, $ANP_{99-124}$; and/or the assay detects $ANP_{99-126}$, but exhibits at least a 5-fold reduction in signal from, and preferably does not appreciably detect, $ANP_{102-124}$.

As described hereinafter, such assays may be designed in a variety of ways known to those of skill in the art. Preferred assays are immunoassays, although other methods are well known to those skilled in the art (for example, the use of biosensors, or the use of natural receptors for natriuretic peptides that are known in the art). Any suitable immunoassay may be utilized, for example, assays which directly detect analyte binding (e.g., by ellipsometric detection), enzyme-linked immunoassays (ELISA), radioimmunoassays (RIAs), competitive binding assays, sandwich immunoassays, and the like. Specific immunological binding of the antibody to the one or more natriuretic peptide fragments can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. Antibodies attached to a second molecule, such as a detectable label, are referred to herein as "antibody conjugates." The skilled artisan will also understand that natural receptors for the natriuretic peptides exist, and that these receptors may also be used in a manner akin to antibodies in providing binding assays.

Immunoassays may be formulated using one or more antibodies selected to bind to an epitope that is partially or completely lost from biologically inactive fragments of the natriuretic peptide as compared to the intact natriuretic peptide. For example, in a sandwich assay, if an antibody bound to a solid phase is selected to bind preferentially to the N-terminal portion of the molecule, and a labeled antibody is selected to bind to the C-terminal portion of the molecule, only those molecules that contain both the N- and C-terminal portions of the molecule will be detected in the assay. Alternatively, both the solid phase and labeled antibodies may be selected to bind to the N-terminal portion of the molecule.

The skilled artisan will understand that cleavage of the natriuretic peptide may remove all of the epitope to which an antibody binds (e.g., the antibody binds to the N-terminal region alone). Alternatively, an epitope may be formed from portions of the natriuretic peptide that are not contiguous in the linear sequence of the molecule, but that are associated in 3-dimensional space in solution, so that epitope comprises more than the described amino acid residues, but removal of the region described amino acid residues results in reduced binding of the antibody, and hence a loss of signal in the assay.

In certain embodiments, antibodies are selected, based not upon a particular affinity for one or more natriuretic peptide(s), but instead based upon a signal that is obtainable in a binding assay such as an immunoassay. The skilled artisan will recognize that various binding assay formats are known in the art, and that it is often the use of antibodies to formulate an appropriate assay that is more important than a particular affinity of an antibody for one or more target molecules. For example, competitive binding assays may comprise a receptor (e.g., an antibody) bound to a solid surface. An analyte of interest in a test sample competes for binding with a labeled molecule that also binds to the receptor. The amount of labeled molecule bound to the receptor (and hence assay signal) is inversely proportional to the amount of analyte of interest in the test sample. In this case, a single antibody attached to the solid phase is used. Alternatively, in a sandwich immunoassay, a first antibody, typically bound to a solid surface, and a second antibody, typically conjugated to a detectable label, each bind to an analyte of interest in a test sample. The amount of labeled molecule bound to the receptor (and hence assay signal) is directly proportional to the amount of analyte of interest in the test sample.

The immunoassays of the present invention are preferably designed to distinguish a biologically active natriuretic peptide from a biologically inactive natriuretic peptide and/or an intact natriuretic peptide from a natriuretic peptide fragment. For example, a preferred immunoassay would distinguish a natriuretic peptide comprising an intact N-terminal region from a fragment of the natriuretic peptide from which the N-terminal region has been lost. An immunoassay is said to "distinguish" between a first group of polypeptides and a second group of polypeptides if the immunoassay provides a signal related to binding of the first group of polypeptides that is at least a factor of 5 greater than a signal obtained from an equal number of molecules of the second group of polypeptides under the same assay conditions, when the assay is performed at no more than twice the amount of the first group of polypeptides necessary to obtain a maximum signal. More preferably, the signal is at least a factor of 10 greater, even more preferably at least a factor of 20 greater, and most preferably at least a factor of 50 greater, at least a factor of 100 greater, or more under such assay conditions. An assay does not "appreciably detect" the second group of polypeptides if a signal related to binding of the first group of polypeptides may be obtained, but no signal above background is obtained from an equal number of molecules of the second group of polypeptides under such assay conditions.

In another aspect, the present invention relates to methods for detecting the presence or amount of a natriuretic peptide in a sample, comprising performing an assay in which the signal depends upon an antibody that specifically binds to a biologically active natriuretic peptide, but that does not specifically bind to biologically inactive fragments of the natriuretic peptide. As discussed above, biologically inactive fragments may include those in which residues from either or both of the N-terminus or C-terminus of the intact natriuretic peptide have been removed, and/or in which the loop formed by intramolecular disulfide bonding of the natriuretic peptide has been cleaved. In preferred embodiments, the assay is performed under conditions in which the signal depends upon an antibody that specifically binds to the intact natriuretic peptide, but that does not specifically bind to a peptide that is generated from the natriuretic peptide when an N-terminal portion of the natriuretic peptide is removed.

In related aspects, the present invention relates to methods for detecting the presence or amount of a natriuretic peptide in a sample, comprising performing an assay in which the signal depends upon an antibody that specifically binds to the intact natriuretic peptide, but that does not specifically bind to fragments of the natriuretic peptide generated when a portion, and preferably at least an N-terminal portion, of the natriuretic peptide is removed.

In various embodiments, the present invention relates to methods for detecting the presence or amount of BNP in a sample, comprising performing an assay in which the signal depends upon an antibody that specifically binds to $BNP_{77-108}$, but that does not specifically bind to $BNP_{94-108}$; the assay depends upon an antibody that specifically binds to $BNP_{77-108}$, but does not specifically bind to $BNP_{90-108}$; the assay depends upon an antibody that specifically binds to $BNP_{77-108}$, but does not specifically bind to $BNP_{81-108}$; the assay depends upon an antibody that specifically binds to $BNP_{77-108}$, but does not specifically bind to $BNP_{79-108}$; the assay depends upon an antibody that specifically binds to $BNP_{77-108}$, but does not specifically bind to BNP77-106; and/or the assay depends upon an antibody that specifically binds to $BNP_{77-108}$, but does not specifically bind to $BNP_{79-106}$.

In various additional embodiments, the present invention relates to methods for detecting the presence or amount of BNP in a sample, comprising performing an assay in which the signal depends upon an antibody that specifically binds to $BNP_{1-76}$, but that does not specifically bind to $BNP_{38-76}$; the assay depends upon an antibody that specifically binds to $BNP_{1-76}$, but does not specifically bind to $BNP_{24-76}$; the assay depends upon an antibody that specifically binds to $BNP_{1-76}$, but does not specifically bind to $BNP_{12-76}$; the assay depends upon an antibody that specifically binds to $BNP_{1-76}$, but does not specifically bind to $BNP_{3-76}$; the assay depends upon an antibody that specifically binds to $BNP_{1-76}$, but does not specifically bind to $BNP_{1-73}$; and/or the assay depends upon an antibody that specifically binds to $BNP_{1-76}$, but does not specifically bind to $BNP_{3-73}$.

In other additional embodiments, the present invention relates to methods for detecting the presence or amount of ANP in a sample, comprising performing an assay in which the signal depends upon an antibody that specifically binds to $ANP_{99-126}$, but that does not specifically bind to $ANP_{113-126}$; the assay depends upon an antibody that specifically binds to $ANP_{99-126}$, but that does not specifically bind to $ANP_{105-126}$; the assay depends upon an antibody that specifically binds to $ANP_{99-126}$, but that does not specifically bind to $ANP_{102-126}$; the assay depends upon an antibody that specifically binds to $ANP_{99-126}$, but that does not specifically bind to $ANP_{99-124}$; and/or the assay depends upon an antibody that specifically binds to $ANP_{99-126}$, but that does not specifically bind to $ANP_{102-124}$.

A signal from an immunoassay is said to "depend upon binding to an antibody" if the antibody participates in formation of a complex necessary to generate the signal. For example, in a sandwich immunoassay formulated using a solid phase antibody and a second antibody conjugate, each of which must bind to an analyte to form the sandwich, each of the solid phase antibody and second antibody participate in formation of the complex necessary to generate the signal. In a competitive immunoassay where a single antibody is used, and an analyte competes with an analyte conjugate for binding, the single antibody participates in formation of the complex necessary to generate the signal. The skilled artisan will understand that numerous additional immunoassay formulations may be provided.

The assay methods described herein may also comprise a step of storing a sample for a period of time prior to assay for one or more natriuretic peptides. Because degradation of natriuretic peptides may be an ongoing process during storage, the storage considerations should be selected to reduce loss of the N-terminal portion of the molecule. Thus, the storage conditions may comprise addition of one or more inhibitors of natriuretic peptide degradation. As discussed hereinafter, the storage conditions may comprise one or more inhibitors of neutral endopeptidase and/or one or more inhibitors of prolyl-specific dipeptidyl peptidase. Such inhibitors are well known in the art. See, e.g., Corti et al., *Circulation* 104: 1856-62, 2001; Senten et al., *J. Comb. Chem.* 5: 336-44, 2003; Senten et al., *Bioorg. Med. Chem. Lett.* 12: 2825-8, 2002. In an alternative or in conjunction with such inhibitors, storage conditions may comprise storage at a reduced temperature, preferably below the freezing point of the sample.

In another aspect, the present invention relates to an assay device configured and arranged to perform the described assays. Devices for performing the assays described herein preferably contain a plurality of discrete, independently addressable locations, or "diagnostic zones," each of which is related to a particular analyte or set of analytes of interest, one or more of which is a natriuretic peptide. For example, each of a plurality of discrete zones may comprise a receptor (e.g., an antibody) for binding a different analyte. Following reaction of a sample with the devices, a signal is generated from the diagnostic zone(s), which may then be correlated to the presence or amount of the peptide of interest.

In yet another aspect, the presence or amount of one or more natriuretic peptide(s) of interest measured by the methods described herein may be related to the presence or absence of a disease, or a disease prognosis (e.g., the likelihood of a future adverse outcome related to a disease). Preferred diseases include various cardiovascular and cerebrovascular diseases, including stroke, congestive heart failure (CHF), cardiac ischemia, systemic hypertension, and/or acute myocardial infarction. These methods preferably comprise determining the presence or amount of one or more natriuretic peptide(s) by the methods described herein, and relating that presence or amount to the disease or prognosis of interest.

In certain embodiments, the signal obtained from an assay need not be related to the presence or amount of one or more natriuretic peptide(s); rather, the signal may be directly related to the presence or absence of a disease, or the likelihood of a future adverse outcome related to a disease. For example, a level of signal x may indicate that y pg/mL of a natriuretic peptide is present in the sample. A table may then indicate that y pg/mL of that natriuretic peptide indicates congestive heart failure. It may be equally valid to simply relate a level of signal x directly to congestive heart failure, without determining how much of the natriuretic peptide is present. Such a signal is preferably obtained from an immunoassay using the antibodies of the present invention, although other methods are well known to those skilled in the art.

In still another aspect, the present invention relates to methods for selecting one or more antibodies for use in an assay for natriuretic peptide(s). These methods comprise selecting antibodies that, when used in an assay, detect a biologically active natriuretic peptide of interest, but that exhibit at least a 5-fold reduction in signal from, and preferably do not appreciably detect, biologically inactive fragments of the natriuretic peptide. As above, biologically inactive fragments may include those in which residues from either or both of the N-terminus or C-terminus of the intact natriuretic peptide have been removed, and/or in which the loop formed by intramolecular disulfide bonding of the natriuretic peptide has been cleaved.

In related aspects, the present invention relates to methods for for selecting one or more antibodies for use in an assay, comprising selecting antibodies that, when used in an assay, detect an intact natriuretic peptide of interest, but that exhibit at least a 5-fold reduction in signal from, and preferably do not appreciably detect, an equimolar amount of a peptide that is generated from the natriuretic peptide when a portion, and preferably an N-terminal portion, of the natriuretic peptide is removed.

In various embodiments, the methods comprise selecting one or more antibodies that detect $BNP_{77-108}$ when used in an assay, but that exhibit at least a 5-fold reduction in signal from, and preferably do not appreciably detect, an equimolar amount of $BNP_{94-108}$; selecting one or more antibodies that detect $BNP_{77-108}$, but that exhibit at least a 5-fold reduction in signal from, and preferably do not appreciably detect, $BNP_{90-108}$; selecting one or more antibodies that detect $BNP_{77-108}$, but that exhibit at least a 5-fold reduction in signal from, and preferably do not appreciably detect, $BNP_{81-108}$; selecting one or more antibodies that detect $BNP_{77-108}$, but that exhibit at least a 5-fold reduction in signal from, and preferably do not appreciably detect, $BNP_{79-108}$; selecting one or more antibodies that detect $BNP_{77-108}$, but that exhibit at least a 5-fold reduction in signal from, and preferably do not appreciably detect, $BNP_{77-106}$; and/or selecting one or more antibodies that detect $BNP_{77-108}$, but that exhibit at least a 5-fold reduction in signal from, and preferably do not appreciably detect, $BNP_{79-106}$.

In various additional embodiments, the methods comprise selecting one or more antibodies that detect $BNP_{1-76}$, when used in an assay, but that exhibit at least a 5-fold reduction in signal from, and preferably do not appreciably detect, an equimolar amount of $BNP_{38-76}$; selecting one or more antibodies that detect $BNP_{1-76}$, but that exhibit at least a 5-fold reduction in signal from, and preferably do not appreciably detect, $BNP_{24-76}$; selecting one or more antibodies that detect $BNP_{31-76}$, but that exhibit at least a 5-fold reduction in signal from, and preferably do not appreciably detect, $BNP_{12-76}$; selecting one or more antibodies that detect $BNP_{1-76}$, but that exhibit at least a 5-fold reduction in signal from, and preferably do not appreciably detect, $BNP_{3-76}$; selecting one or more antibodies that detect $BNP_{1-76}$, but that exhibit at least a 5-fold reduction in signal from, and preferably do not appreciably detect, $BNP_{1-73}$; and/or selecting one or more antibodies that detect $BNP_{1-76}$, but that exhibit at least a 5-fold reduction in signal from, and preferably do not appreciably detect, $BNP_{3-73}$.

In other additional embodiments, the methods comprise selecting one or more antibodies that detect $ANP_{99-126}$ when used in an assay, but that exhibit at least a 5-fold reduction in signal from, and preferably do not appreciably detect, an equimolar amount of $ANP_{113-126}$; selecting one or more antibodies that detect $ANP_{99-126}$ when used in an assay, but that exhibit at least a 5-fold reduction in signal from, and preferably do not appreciably detect, an equimolar amount of $ANP_{105-126}$; selecting one or more antibodies that detect $ANP_{99-126}$ when used in an assay, but that exhibit at least a 5-fold reduction in signal from, and preferably do not appreciably detect, an equimolar amount of $ANP_{101-126}$; selecting one or more antibodies that detect $ANP_{99-126}$ when used in an assay, but that exhibit at least a 5-fold reduction in signal from, and preferably do not appreciably detect, an equimolar amount of $ANP_{99-124}$; and/or selecting one or more antibodies that detect $ANP_{99-126}$ when used in an assay, but that exhibit at least a 5-fold reduction in signal from, and preferably do not appreciably detect, an equimolar amount of $ANP_{101-124}$.

In other related aspects, the present invention relates to a method of selecting one or more antibodies for use in an assay for natriuretic peptide(s). The methods comprise selecting one or more antibodies that specifically bind to a biologically active natriuretic peptide, but that do not specifically bind to biologically inactive fragments of the natriuretic peptide. As discussed above, biologically inactive fragments may include those in which residues from either or both of the N-terminus or C-terminus of the intact natriuretic peptide have been removed, and/or in which the loop formed by intramolecular disulfide bonding of the natriuretic peptide has been cleaved. In preferred embodiments, the assay is performed under conditions in which the signal depends upon an antibody that specifically binds to the intact natriuretic peptide, but that does not specifically bind to a peptide that is generated from the natriuretic peptide when an N-terminal portion of the natriuretic peptide is removed In still other related aspects, the present invention relates to methods for selecting one or more antibodies for use in an assay, comprising selecting antibodies that specifically bind to the intact natriuretic peptide, but that do not specifically bind to biologically inactive fragments of the natriuretic peptide generated when an N-terminal portion of the natriuretic peptide is removed.

In various embodiments, the methods comprise selecting one or more antibodies that specifically bind to $BNP_{77-108}$, but that do not specifically bind to $BNP_{94-108}$; selecting one or more antibodies that specifically bind to $BNP_{77-408}$, but that do not specifically bind to $BNP_{90-108}$; selecting one or more antibodies that specifically bind to $BNP_{77-108}$, but that do not specifically bind to $BNP_{81-108}$; selecting one or more antibodies that specifically bind to $BNP_{77-108}$, but that do not specifically bind to $BNP_{79-108}$; selecting one or more antibodies that specifically bind to $BNP_{77-108}$, but that do not specifically bind to $BNP_{77-106}$; and/or selecting one or more antibodies that specifically bind to $BNP_{77-108}$, but that do not specifically bind to $BNP_{79-106}$.

In various additional embodiments, the methods comprise selecting one or more antibodies that specifically bind to $BNP_{1-76}$, but that do not specifically bind to $BNP_{38-76}$; selecting one or more antibodies that specifically bind to $BNP_{1-76}$, but that do not specifically bind to $BNP_{24-76}$; selecting one or more antibodies that specifically bind to $BNP_{1-76}$, but that do not specifically bind to $BNP_{12-76}$; selecting one or more antibodies that specifically bind to $BNP_{1-76}$, but that do not specifically bind to $BNP_{3-76}$;

selecting one or more antibodies that specifically bind to $BNP_{1-76}$, but that do not specifically bind to $BNP_{1-73}$; and/or selecting one or more antibodies that specifically bind to $BNP_{1-76}$, but that do not specifically bind to $BNP_{3-73}$.

In other additional embodiments, the methods comprise selecting one or more antibodies that specifically bind to $ANP_{99-126}$, but that do not specifically bind to $ANP_{113-126}$; selecting one or more antibodies that specifically bind to $ANP_{99-126}$, but that do not specifically bind to $ANP_{105-126}$; selecting one or more antibodies that specifically bind to $ANP_{99-126}$, but that do not specifically bind to $ANP_{101-126}$; selecting one or more antibodies that specifically bind to $ANP_{99-126}$, but that do not specifically bind to $ANP_{99-124}$; and/or selecting one or more antibodies that specifically bind to $ANP_{99-126}$, but that do not specifically bind to $ANP_{101-124}$.

In another aspect, one or more antibodies and/or antibody conjugates of the present invention may be provided as kits for determining the presence or amount of natriuretic peptide(s). These kits preferably comprise devices and reagents for performing at least one assay as described herein on a test sample. Such kits preferably contain sufficient reagents to perform one or more such determinations, and/or Food and Drug Administration (FDA)-approved labeling.

In still another aspect, the invention relates to methods for determining a treatment regimen for use in a patient. The methods preferably comprise determining the presence or amount of one or more natriuretic peptide(s) by the methods described herein, and relating this presence or amount to a disease or prognostic state. As discussed herein, diagnosis and differentiation of various cardiovascular and cerebrovascular diseases, including stroke, congestive heart failure (CHF), cardiac ischemia, systemic hypertension, acute coronary syndrome, and/or acute myocardial infarction may be related to ANP, BNP, and/or CNP levels. Once a diagnosis or prognosis is obtained, a treatment regimen is selected to be consistent with that diagnosis.

It is another object of the invention to provide compositions and methods for stabilizing natriuretic peptides. Such methods may improve the therapeutic potential of natriuretic peptides, particularly for the treatment of cardiovascular diseases. Several natriuretic peptides, including pro-BNP, mature BNP, and pro-ANP comprise a penultimate proline residue, and are suitable substrates for prolyl-specific dipeptidyl dipeptidases ("DPPs"). Thus, while mature BNP has been reported to exhibit resistance to degradation by neutral endopeptidase relative to ANP, DPPs may represent a previously unrecognized degradation pathway for the mature BNP molecule as well as for pro-BNP and pro-ANP. Furthermore, the removal of the proline-containing dipeptide may open the various natriuretic peptides to further degradation by other peptidases. Subjects that may benefit from increased natriuretic peptide concentrations may be treated with inhibitors of one or more DPPs, either alone or in combination with neutral endopeptidase inhibitors, and/or treated with natriuretic peptides and/or natriuretic peptide analogs exhibiting increased DPP stability. In addition, BNP in samples removed from a subject may be stabilized during storage using these same inhibitors.

Thus, in one aspect, the present invention relates to methods of inhibiting degradation of one or more natriuretic peptides. The method comprises administering one or more inhibitors of prolyl-specific DPP in an amount sufficient to inhibit degradation of the natriuretic peptide.

In another aspect, the present invention relates to methods for treating a subject in need of increased natriuretic peptide function, preferably subjects suffering from heart failure. The methods comprise administering one or more inhibitors of prolyl-specific DPP to the subject, preferably in an amount sufficient to inhibit degradation of the natriuretic peptide.

In certain embodiments, the inhibitor(s) of prolyl-specific DPP are selective for one or more DPP(s) for which pro-BNP, mature BNP, and/or pro-ANP are a substrate. Methods for designing and selecting specific DPP inhibitors are well known in the art. See, e.g., Leiting et al., *Biochem. J.* 371: 525-32, 2003; Sedo et al., *Physiol. Res.* 52: 367-72, 2003; Villhauer et al., *J. Med. Chem.* 46: 2774-89, 2003; Senten et al., *J. Comb. Chem.* 5: 336-44, 2003; Senten et al., *Bioorg. Med. Chem. Lett.* 12: 2825-8, 2002; Borloo and Meester, *Verh. K. Acad. Geneeskd. Belg.* 56: 57-88, 1994. In addition, DPP may be inhibited at the level of expression by methods known to those of skill in the art, such as by antisense or RNAi constructs. DPPs may also be inhibited through the use of binding proteins, e.g., antibodies or fragments thereof that specifically bind to one or more DPPs and prevent their activity on a natriuretic peptide substrate.

The methods described herein may comprise the use of one or more inhibitors of prolyl-specific DPP alone, or such inhibitors may be combined with one or more inhibitors of neutral endopeptidase and/or other protease inhibitors, and/or with one or more exogenously added natriuretic peptides to provide a potentiated increase in natriuretic peptide function to the subject in comparison to the use of inhibitors of neutral endopeptidase and/or exogenously added natriuretic peptides in the absence of prolyl-specific DPP inhibitor(s). These compounds may be conveniently provided as part of a pharmaceutical composition.

In preferred embodiments, subjects receiving the treatment methods described herein suffer from diseases selected from the group consisting of stroke, congestive heart failure (CHF), cardiac ischemia, systemic hypertension, and/or acute myocardial infarction. In particularly preferred embodiments, subjects receiving the treatment methods described herein are selected on the basis of a BNP level. For example, subjects may be selected on the basis of a plasma BNP level prior to receiving treatment of at least about 80 pg/mL, preferably at least about 100 pg/mL, still more preferably at least about 200 pg/mL, yet more preferably at least about 500 pg/mL, and most preferably at least about 1000 pg/mL.

In yet another aspect, the present invention relates to methods for treating a subject in need of increased natriuretic peptide function comprising administering one or more analogues of a natriuretic peptide that provide increased stability in the presence of prolyl-specific DPP (e.g. as measured by an increase in the $t_{1/2}$ of the natriuretic peptide of interest in the blood of the subject).

It is yet another object of the invention to provide methods and compositions for determining the presence or amount of one or more natriuretic peptides of interest, where one or more of those natriuretic peptides of interest are glycosylated. Covalently bound carbohydrate residues in glycosylated natriuretic peptides can have substantial effects on the ability of various assay methods to detect such peptides. By careful selection of assay conditions, such effects can be mitigated, resulting in an assay result that is representative of the presence or amount of the natriuretic peptides of interest in a sample.

Thus, in another aspect, the present invention relates to methods for detecting the presence or amount of one or more natriuretic peptides of interest in a sample, where one or more of those natriuretic peptides comprise covalently bound carbohydrate residues. These methods comprise removing one or more covalently bound carbohydrate residues from one or more of said natriuretic peptides of interest, and assaying the sample for the natriuretic peptides of interest. The assay result is thus related to the presence or amount of said natriuretic peptides of interest in said sample. In various embodiments, the covalently bound carbohydrate residues may be removed from one or more naturietic peptides by enzymatic treatment of the peptides, by non-enzymatic chemical treatment of the peptides, or by a combination of these methods.

Effective enzymatic methods for removing N- and O-linked carbohydrate residues are well known in the art, using enzymes such as N-glycanase (also known as N-glycosidase), endoglycosidase H, endoglycosidase A, O-glycanase (also known as endo-α-N-acetylgalactosaminidase), α2-(3,6,8,9)-neuriminidase, β(1,4)-galactosidase, N-acetylglucosaminidase, endoglycosidase $F_1$, endoglycosidase $F_2$, and/or endoglycosidase $F_3$. This list is not meant to be limiting.

In the case of non-enzymatic chemical treatments for removal of covalently bound carbohydrate residues from peptides, hydrazine hydrolysis has been found to be effective in the release of unreduced O- and N-linked oligosaccharides. Selective and sequential release of oligosaccharides can be accomplished by initial mild hydrazinolysis of the O-linked oligosaccharides at about 60° C. followed by N-linked oligosaccharides at about 95° C. See, e.g., Patel and Rarekh, *Meth. Enzymol.* 230, 58-66, 1994. Such treatment may result in destruction of the polypeptide however. Alkaline-β-elimination of O-linked oligosaccharides, which utilizes alkaline sodium borohydride in a mild base environment, may be preferred. See, e.g., *Glycobiology: A Practical Approach*, Fukuda, M. and Kobata, A. (Eds), pp. 291-328, IRL/Oxford Univ. Press, Oxford, 1993. In addition, Trifluoromethanesulfonic acid hydrolysis may be employed. This method typically leaves an intact polypeptide, but results in destruction of the glycan. See, e.g., Edge, *Biochem.* 1 376: 339-50, 2003.

The foregoing methods of sugar removal from peptides may be used on native (non-denatured) polypeptides and/or following denaturation of the polypeptides. Whether enzymatic, non-enzymatic, or both treatments are employed to remove covalently bound carbohydrate residues from natriuretic peptides, it is preferred that at least about 50%, more preferably, at least about 60%, still more preferably at least about 70%, yet more preferably at least about 80%, and most preferably at least about 90% to about 100% of the carbohydrate residues are removed from one or more, and preferably all, of the glycosylated natriuretic peptides of interest by this treatment. The extent of glycosylation of a polypeptide can be determined by comparing the apparent mass of the polypeptide to the mass of the amino acid constituents of the polypeptide, and assuming that the balance of the apparent mass is contributed by glycosylation. In the event that other modifications (e.g., oxidation, nitration, phosphorylation) are known to have occurred, the mass contributed by these other modifications may also be subtracted from the apparent mass. The extent of carbohydrate residue removal can then be monitored by determining the apparent mass of the polypeptide following deglycosylation treatment. Methods for determining the apparent mass of a polypeptide (e.g., SDS gel electrophoresis, analytical centrifugation, gel permeation chromatography, mass spectrometry, etc.) are well known to those of skill in the art.

The sample containing such glycosylated natriuretic peptides may be a test sample as that term is defined herein. The glycosylated natriuretic peptides present in such a sample may be naturally present, such as in a sample obtained from a patient, or may be a standard sample. Natriuretic peptides used in formulating such standards are often expressed recombinantly in mammalian tissue culture systems, which contain active glycosylation functions.

Following the deglycosylation step, the methods described herein may employ any assay methods known in the art. Such assay methods may employ separation methods such as affinity separation, gel electrophoresis, capillary electrophoresis, liquid chromatography, and/or HPLC to separate analytes of interest for detection. In preferred embodiments, immunoassay devices and methods are often used for affinity separation, in various sandwich, competitive, or non-competitive assay formats, to generate a signal that is related to the presence or amount of one or more natriuretic peptides of interest. Additionally, certain methods and devices, such as biosensors and optical immunoassays, may be employed to determine the presence or amount of analytes without the need for a labeled molecule.

In addition, mass spectrometry methods may advantageously be employed as part of the assay method. The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Molecules (e.g., peptides) in a test sample can be ionized by any method known to the skilled artisan. These methods include, but are not limited to, electron ionization, chemical ionization, fast atom bombardment, field desorption, and matrix-assisted laser desorption ionization ("MALDI"), surface enhanced laser desorption ionization ("SELDI"), photon ionization, electrospray, and inductively coupled plasma.

In certain embodiments, the MS methods discussed above are preferably combined with an affinity purification step such as binding to an antibody that specifically binds one or more polypeptides of interest. See, e.g., Nelson et al., *Anal. Chem.*, 67: 1153, 1995; Tubbs et al., *Anal. Biochem.* 289: 26, 2001. Niederkofler et al., *Anal. Chem.* 73: 3294, 2001.

One feature of glycoproteins is the typical heterogeneity of the glycans. It is very common for individual molecules of a given glycoprotein to carry different carbohydrates at the same attachment site in the polypeptide chain. Any structural changes in the carbohydrate residues will result in the formation of discrete molecular subsets referred to as glycoforms. In the case of various separation methods, such heterogeneity can substantially complicate the analysis due to differences in charge and mass of the various polypeptides of interest and/or differences in the binding of the various polypeptides of interest to a binding matrix (e.g., an antibody). In addition, carbohydrates are not ionized as efficiently as compounds such as proteins that can be easily protonated; neither do they appear to be transferred to the vapor phase as effectively.

Thus, in preferred embodiments, the methods described herein provide an increased detection of one or more natriuretic peptides of interest, as compared to performing the same assaying step in the absence of removing one or more covalently bound carbohydrate residues from one or more of the natriuretic peptides of interest. The term "increased detection" as used herein refers to an increased signal obtained from the assay method for one or more particular naturietic peptides of interest. Such an increased signal may be representative of an increased ability to detect all of the naturietic peptides of interest. For example, an antibody that could not bind certain glycosylated forms of one or more naturietic peptides of interest would result in an assay signal that underestimates the concentration of those naturietic peptides; or less efficient ionization of certain glycosylated forms of one or more naturietic peptides of interest would result in an assay signal by MS that underestimates the concentration of those naturietic peptides. Deglycosylation can result in an increased assay signal. Such an increased signal may also be representative of an increased ability to detect one or more specific forms of the naturietic peptides of interest. For example, the heterogeneity of the glycans may result in separation of a single polypeptide into a plurality of different fractions in a separation method (e.g., those based on mass and/or charge). Deglycosylation can result in coalescence of those different fractions into a single fraction, thus providing an improved assay signal for that fraction.

In various embodiments, the increased detection of one or more naturietic peptides of interest, as compared to performing the same assaying step in the absence of removing one or more covalently bound carbohydrate residues from one or more of the natriuretic peptides of interest, is measured by an assay signal that increases by at least about 5%, more preferably at least about 10%, still more preferably at least about 20%, even more preferably at least about 50%, still more preferably at least about 100%, and most preferably at least about 200% or more.

In particularly preferred embodiments, the natriuretic peptides of interest are BNP and/or one or more of its related fragments. The term "related fragments" is defined hereinafter. Preferred BNP-related fragments comprise those selected from the group consisting of pro-BNP (BNP$_{1-108}$), NT-proBNP (BNP$_{1-76}$), BNP$_{3-108}$, BNP$_{3-76}$, and BNP$_{79-108}$. This list is not meant to be limiting.

In a related aspect, the present invention relates to methods for selecting and using antibodies that are either sensitive or insensitive to the presence (or absence) of covalently bound carbohydrate residues on one or more natriuretic peptides of interest. Antibodies may be screened for the ability to bind to one or more glycosylated natriuretic peptides of interest, and that binding may be compared to the ability to bind to one or more natriuretic peptides of interest following removal of one or more covalently bound carbohydrate residues. Those antibodies that provide substantially identical binding by this measure represent "insensitive" antibodies. Those antibodies that provide binding by this measure that is not substantially identical for glycosylated or deglycosylated forms represent "sensitive" antibodies. Such antibodies may be selected for use in assay methods for the detection of one or more natriuretic peptides of interest.

The term "removal of one or more covalently bound carbohydrate residues" in this context does not necessarily refer to the use of enzymatic or non-enzymatic chemical treatments to remove existing carbohydrate residues from a polypeptide. Instead, it is meant to encompass any method for generating a polypeptide lacking one or more covalently bound carbohydrate residues. For example, solid phase synthesis methods may be used to generate a polypeptide that is free of all carbohydrate residues for use in such antibody screening methods. It is preferred that at least about 50%, more preferably at least about 60%, still more preferably at least about 70%, yet more preferably at least about 80%, and most preferably at least about 90% to about 100% of the carbohydrate residues are removed from one or more, and preferably all, of the glycosylated natriuretic peptides of interest for use in the screening methods described herein.

The term "substantially identical binding" refers to an antibody that, when used in an assay, provides signals that are within a factor of about 2 of one another in the screening comparison described above. A factor of 1 indicates that the signals are equal; that signals are within a factor of 2 indicates that one signal is less than or equal to the other signal×2. Preferably, antibodies exhibiting substantially identical binding provide signals that are within a factor of about 1.75, more preferably within a factor of about 1.5, still more preferably within a factor of about 1.25, and most preferably within a factor of about 1.1 to 1.

Such antibodies may also have "substantially identical affinity" for one or more glycosylated natriuretic peptides of interest, as compared to one or more natriuretic peptides of interest following removal of one or more covalently bound carbohydrate residues. A factor of 1 indicates that the affinities are equal; that affinities are within a factor of 2 indicates that one affinity is less than or equal to the other signal×2. Preferably, antibodies exhibiting substantially identical binding provide affinities that are within a factor of about 1.75, more preferably within a factor of about 1.5, still more preferably within a factor of about 1.25, and most preferably within a factor of about 1.1 to 1.

The summary of the invention described above is non-limiting and other features and advantages of the invention will be apparent from the following detailed description of the invention, and from the claims.

BRIEF DESCRIPTION OF THE FIGURES

FIG. 1 shows a mass spectrum of BNP and its degradation products in human serum in the absence (panels A and C) and the presence (panels B and D) of an inhibitor of dipeptidyl peptidase.

DETAILED DESCRIPTION OF THE INVENTION

The present invention relates in part to methods for distinguishing between biologically active (e.g., full length) natriuretic peptides from biologically inactive forms of the natriuretic peptides. As described herein, antibodies may be generated that selectively recognize biologically active natriuretic peptides, and used in assays that exhibit reduced inaccuracies caused by the presence of inactive natriuretic peptide fragments present in a sample.

The term "natriuretic peptide" as used herein refers to members of a group of naturally occurring polypeptide hormones that act in the body to oppose the activity of the renin-angiotensin system, and their biosynthetic precursors and biologically active fragments. There are three major human natriuretic peptides: atrial natriuretic peptide (ANP), which is synthesized in the atria; brain-type natriuretic peptide (BNP), which is synthesized in the ventricles; and C-type natriuretic peptide (CNP), which is synthesized in the brain.

The term "intact natriuretic peptide" as used herein refers to the full length pre-pro-natriuretic peptide, full length pro-natriuretic peptide, full length mature natriuretic peptide, and/or the full length portions removed during processing of the pre-pro- or pro-natriuretic peptides during biosynthesis. In the case of BNP for example, the term "intact natriuretic peptides" encompasses the full length 32 amino acid mature BNP hormone; the full length 134-amino acid pre-pro-BNP molecule; the full length 108-amino acid pro- BNP molecule; the full length 76-amino acid NT-pro BNP molecule, and/or the full length 26-amino acid "pre" peptide.

The sequence of the human 108 amino acid BNP precursor pro-BNP ($BNP_{1-108}$) is shown as SEQ ID NO: 1. Mature, full length BNP ($BNP_{77-108}$) is shown underlined:

```
                                                       (SEQ ID NO: 1)
HPLGSPGSAS DLETSGLQEQ RNHLQGKLSE LQVEQTSLEP LQESPRPTGV    50

WKSREVATEG IRGHRKMVLY TLRAPRSPKM VQGSGCFGRK MDRISSSSGL   100

GCKVLRRH.                                               108
```

Human $BNP_{1-108}$ is synthesized as a larger precursor pre-pro-BNP having the sequence shown as SEQ ID NO: 2 (with the "pre" sequence shown in bold):

```
                                                       (SEQ ID NO: 2)
MDPQTAPSRA LLLLLFLHLA FLGGRSHPLG SPGSASDLET SGLQEQRNHL    50

QGKLSELQVE QTSLEPLQES PRPTGVWKSR EVATEGIRGH RKMVLYTLRA   100

PRSPKMVQGS GCFGRKMDRI SSSSGLGCKV LRRH.                  134
```

The sequence of the 126 amino acid human ANP precursor pro-ANP ($ANP_{1-126}$) is shown as SEQ ID NO: 3, with mature, full length ANP ($ANP_{99-126}$) underlined:

```
                                                       (SEQ ID NO: 3)
NPMYNAVSNA DLMDFKNLLD HLEEKMPLED EVVPPQVLSD PNEEAGAALS    50

PLPEVPPWTG EVSPAQRDGG ALGRGPWDSS DRSALLKSKL RALLTAPRSL   100

RRSSCFGGRM DRIGAQSGLG CNSFRY.                           126
```

Human $ANP_{1-126}$ is synthesized as a larger precursor pre-pro-ANP having the sequence shown in SEQ ID NO: 4 (with the "pre" sequence shown in bold):

```
                                                       (SEQ ID NO: 4)
MSSFSTTTVS FLLLLAFQLL GQTRANPMYN AVSNADLMDF KNLLDHLEEK    50

MPLEDEVVPP QVLSDPNEEA GAALSPLPEV PPWTGEVSPA QRDGGALGRG   100

PWDSSDRSAL LKSKLRALLT APRSLRRSSC FGGRMDRIGA QSGLGCNSFR   150

Y.                                                      151
```

The sequence of the 126 amino acid human CNP precursor pro-CNP ($CNP_{1-126}$) is shown as SEQ ID NO: 5, with the full length mature CNP form CNP-53 ($CNP_{74-126}$) shown in italics, and the full length mature CNP form CNP-22 ($CNP_{105-126}$) shown underlined:

```
                                                       (SEQ ID NO: 5)
MHLSQLLACA LLLTLLSLRP SEAKPGAPPK VPRTPPAEEL AEPQAAGGGQ    50

KKGDKAPGGG GANLKGDRSR LLRDLRVDTK SRAAWARLLQ EHPNARKYKG   100

ANKKGLSKGC FGLKLDRIGS MSGLGC.                           126
```

The term "fragment" as used herein refers to a polypeptide that comprises at least six contiguous amino acids of a polypeptide from which the fragment is derived, but is less than the complete parent polypeptide. Thus, a fragment of pro-BNP ($BNP_{1-108}$) refers to a polypeptide that comprises at least six contiguous amino acids of $BNP_{1-108}$; a fragment of mature BNP refers to a polypeptide that comprises at least six contiguous amino acids of $BNP_{77-108}$; a fragment of the polypeptide generated by cleavage of pro-BNP into mature BNP refers to a polypeptide that comprises at least six contiguous amino acids of $BNP_{1-76}$. Similarly, a fragment of pro-ANP ($ANP_{1-126}$) refers to a polypeptide that comprises at least six contiguous amino acids of $ANP_{1-126}$; a fragment of mature ANP refers to a polypeptide that comprises at least six contiguous amino acids of $ANP_{99-126}$; a fragment of the polypeptide generated by cleavage of pro-ANP into mature ANP refers to a polypeptide that comprises at least six contiguous amino acids of $BNP_{1-98}$; and a fragment of pro-CNP ($CNP_{1-126}$) refers to a polypeptide that comprises at least six contiguous amino acids of $CNP_{1-126}$; a fragment of mature CNP refers to a polypeptide that comprises at least six contiguous amino acids of $CNP_{74-126}$ or $CNP_{105-126}$, a fragment of the polypeptide generated by cleavage of pro-CNP into mature CNP refers to a polypeptide that comprises at least six contiguous amino acids of $CNP_{1-73}$ or $CNP_{1-104}$. In preferred embodiments, a fragment refers to a polypeptide that comprises at least 10 contiguous amino acids of a polypeptide from which the fragment is derived; at least 15 contiguous amino acids of a polypeptide from which the fragment is derived; or at least 20 contiguous amino acids of a polypeptide from which the fragment is derived.

The term "related fragment" as used herein refers to one or more fragments of a particular polypeptide or its biosynthetic parent that may be detected as a surrogate for the polypeptide itself or as independent markers. For example, human BNP is derived by proteolysis of a 108 amino acid precursor molecule, referred to hereinafter as $BNP_{1-108}$. Mature SNP, or "the BNP natriuretic peptide," or "BNP-32" is a 32 amino acid molecule representing amino acids 77-108 of this precursor, which may be referred to as $BNP_{77-108}$. The remaining residues 1-76 are referred to hereinafter as $BNP_{1-76}$. $BNP_{1-108}$ and $BNP_{1-76}$ are examples of "BNP-related fragments."

The term "fragment formed by removal of an N-terminal portion" as used herein in reference to natriuretic peptide fragments refers to a fragment of an intact natriuretic peptide formed by removal of one or more amino acids from the amino terminal end of the intact peptide. In preferred embodiments, such a fragment is formed by removal of at least 2, 3, 4, 5, 7, 10, 15, 20, or more amino acids from the amino terminal end of the intact peptide.

The term "biologically active" as used herein in reference to natriuretic peptides and fragments thereof refers to a full length mature natriuretic peptide; or a polypeptide derived from the full length mature natriuretic peptide or its precursor molecules that exhibit at least 50% of the vasorelaxation effects in isolated preconstricted mouse aortic rings exhibited by the full length mature natriuretic peptide, measured as described in Lopez et al., *J. Biol. Chem.* 272: 23064-23068, 1997. Biologically active natriuretic peptides may include fragments of the full length mature natriuretic peptide, or precursor forms or fragments thereof.

The term "biologically inactive" as used herein in reference to natriuretic peptide fragments refers to a polypeptide derived from the full length mature natriuretic peptide or its precursor that is not "biologically active" as defined above. As used herein, the term "biologically inactive" does not necessarily refer to a complete loss of all biological activity. Rather, a "biologically inactive" natriuretic peptide fragment preferably exhibits less than 50%, preferably less than 25%, more preferably less than 10%, and most preferably less than 1%, of one or more biological functions of the intact natriuretic peptide. This biological function may be receptor binding, which may be measured as described in Smith et al., *J. Endocrinal.* 167: 23946, 2000, cGMP production in cultured rat aortic smooth muscle cells, which may be measured as described in Shimekake et al., *FEBS Lett.* 309: 185-9, 1992, and/or the vasorelaxation effects in isolated preconstricted mouse aortic rings exhibited by the full length mature natriuretic peptide, measured as described in Lopez et al., *J Biol. Chem.* 272: 23064-23068, 1997, compared to that exhibited by the full length mature natriuretic peptide.

The term "glycosylated" as used herein in regard to polypeptides refers to polypeptides comprising covalently bound sugar units, often in the form of glycan chains. The individual sugar units are referred to herein as "covalently bound carbohydrate residues." Glycosylation of polypeptides in eukaryotics occurs principally through glycosidic bonds to an asparagine side chain ("N-linked"); through glycosidic bonds to to serine or threonine side chains ("O-linked"); or the polypeptide may be linked to a phosphatidylinositol lipid anchor through a carbohydrate bridge ("GPI-linked").

The term "deglycosylation" as used herein refers to methods for removing one or more covalently bound carbohydrate residues from polypeptides. While removal of all covalently bound carbohydrate residues is preferred, a polypeptide is considered to have been deglycosylated if any covalently bound carbohydrate residues have been removed. Enzymatic treatments, non-enzymatic treatments, or a combination of the two may be employed to remove covalently bound carbohydrate residues from polypeptides. It is preferred that at least about 50%, more preferably, at least about 60%, still more preferably at least about 70%, yet more preferably at least about 80%, and most preferably at least about 90% to about 100% of the carbohydrate residues are removed from a polypeptide.

As used herein, the term "purified" in reference to polypeptides does not require absolute purity. Instead, it represents an indication that the polypeptide(s) of interest is(are) in a discrete environment in which abundance (on a mass basis) relative to other proteins is greater than in a biological sample. By "discrete environment" is meant a single medium, such as a single solution, a single gel, a single precipitate, etc. Purified polypeptides may be obtained by a number of methods including, for example, laboratory synthesis, chromatography, preparative electrophoresis, centrifugation, precipitation, affinity purification, etc. One or more "purified" polypeptides of interest are preferably at least 10% of the protein content of the discrete environment. One or more "substantially purified" polypeptides are at least 50% of the protein content of the discrete environment, more preferably at least 75% of the protein content of the discrete environment, and most preferably at least 95% of the protein content of the discrete environment. Protein content is determined using a modification of the method of Lowry et al., *J. Biol. Chem.* 193: 265, 1951, described by Hartree, *Anal Biochem* 48: 422-427 (1972), using bovine serum albumin as a protein standard.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, P Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies, monoclonal antibodies, polyclonal antibodies, and antibodies obtained by molecular biological techniques (e.g., by phage display methods) are also included by reference in the term "antibody." Preferred antibodies are "Omniclonal" antibodies. By this is meant a mixture of different antibody molecules selected from a phage display library, where each antibody specifically binds to a target antigen with a minimum affinity of $10^9$ $M^{-1}$ to $10^1$ $M^{-1}$.

The term "specifically binds" is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ M. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$.

Affinity is calculated as $K_d = k_{off}/k_{on}$ ($K_{off}$ is the dissociation rate constant, $K_{on}$ is the association rate constant and $K_d$ is the equilibrium constant. Affinity can be determined at equilibrium by measuring the fraction bound (r) of labeled ligand at various concentrations (c). The data are graphed using the Scatchard equation:

$$r/c = K(n-r):$$

where
r=moles of bound ligand/mole of receptor at equilibrium;
c=free ligand concentration at equilibrium;
K=equilibrium association constant; and
n=number of ligand binding sites per receptor molecule
By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1\times10^{-6}$ moles/liter, is more preferably at least about $1\times10^{-7}$ moles/liter, is even more preferably at least about $1\times10^{-8}$ moles/liter, is yet even more preferably at least about $1\times10^{-9}$ moles/liter, and is most preferably at least about $1\times10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "discrete" as used herein refers to areas of a surface that are non-contiguous. That is, two areas are discrete from one another if a border that is not part of either area completely surrounds each of the two areas. The term "independently addressable" as used herein refers to discrete areas of a surface from which a specific signal may be obtained. One skilled in the art will appreciate that antibody zones can also be independent of each other, but can be in contact with each other on a surface.

The term "test sample" as used herein refers to a sample in which the presence or amount of one or more analytes of interest are unknown and to be determined in an assay, preferably an immunoassay. Preferably, a test sample is a bodily fluid obtained for the purpose of diagnosis, prognosis, or evaluation of a subject, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components. Preferred samples may be obtained from bacteria, viruses and animals, such as dogs and cats. Particularly preferred samples are obtained from humans. By way of contrast, a "standard sample" refers to a sample in which the presence or amount of one or more analytes of interest are known prior to assay for the one or more analytes.

The term "disease sample" as used herein refers to a tissue sample obtained from a subject that has been determined to suffer from a given disease. Methods for clinical diagnosis are well known to those of skill in the art. See, e.g., *Kelley's Textbook of Internal Medicine*, 4th Ed., Lippincott Williams & Wilkins, Philadelphia, Pa., 2000; *The Merck Manual of Diagnosis and Therapy*, 17th Ed., Merck Research Laboratories, Whitehouse Station, N.J., 1999.

The terms "prolyl-specific dipeptidyl peptidase" or "prolyl-specific DPP" refer to serine proteases that cleave dipeptides from the N-terminal of substrate polypeptides, and that exhibit a preference for proline in the second position (i.e., NH2-X-pro-peptide-COOH, where X is an amino acid, and the bond between pro and the remaining peptide is cleaved). Such proteases are generally classified under E.C.3.4.14.X, including E.C.3.4.14.5 and 3.4.14.11. DPPs are often classified into types such as DPP-II and DPP-IV.

The term "inhibitor" as used herein in reference to molecules that affect an enzymatic (e.g., proteolytic) activity does not necessarily refer to a complete loss of all enzymatic activity. Rather, an "inhibitor" reduces an enzymatic activity by at least 10%, more preferably at least 25%, even more preferably by at least 50%, still more preferably by at least 75%, and most preferably by at least 90%, of the enzymatic activity exhibited in the absence of the inhibitor. In vitro, the activity of an inhibitor may be measured by directly measuring enzymatic activity by methods well known to those of skill in the art. In vivo, the activity of an inhibitor may also be measured by directly measuring enzymatic activity on the enzyme substrate, or in the case of a degradative enzyme, may be measured by determining a time ($T_{1/2}$) in which ½ of the substrate is cleared from the body of a subject (e.g., an experimental animal). In the latter case, an "inhibitor" increases a $T_{1/2}$ by at least 10%, more preferably at least 25%, even more preferably by at least 50%, still more preferably by at least 75%, and most preferably by at least 90%, compared to the $T_{1/2}$ exhibited in the absence of the inhibitor.

Preferred inhibitors are selective for a particular class of proteases (e.g., selective for dipeptidyl peptidase or for a particular subset of dipeptidyl peptidase). An inhibitor is said to be "selective" for a particular class of protease if it inhibits that class at least 10-fold more, more preferably at least 100-fold more, and most preferably at least 1000-fold more, than non-target proteases. Selective inhibitors of various DPP types are known. For example, H-Dab-Pip is reportedly be selective (>7,600-fold) for dipeptidyl peptidase II (DPP II; EC 3.4.14.2) over DPP IV ($IC_{50}$>1 mM) (DPP IV; EC 3.4.14.5). Senten et al., *Bioorg. Med. Chem. Lett.* 12: 2825, 2002. Similarly, 1-[[[2-[(5-cyanopyridin-2-yl)amino]ethyl]amino]acetyl]-2-cyano-(S)-pynrolidine is reportedly a selective, orally active inhibitor of DPP IV. Ahren et al., *Diabetes Care* 25:869-75, 2002.

The term "about" as used herein refers to +/−10% of a given number.

Use of Natriuretic Peptide Fragments as Prognostic and Diagnostic Markers

As noted above, increased blood levels of natriuretic peptides have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; WO 03/016910; Hunt et al., *Biochem. Biophys. Res. Comm.* 214: 1175-83 (1995); Venugopal, *J. Clin. Pharm. Ther.* 26: 1531, 2001; and Kalra et al., *Circulation* 107: 571-3, 2003; each of which is hereby incorporated in its entirety, including all tables, figures, and claims. The natriuretic peptides, alone, collectively, and/or together with additional proteins, can also serve as disease markers and indicators of prognosis in various cardiovascular conditions.

It has been reported that removal of natriuretic peptides from the circulation involves degradation pathways. Indeed, inhibitors of neutral endopeptidase, which cleaves natriuretic peptides under certain circumstances, have been suggested to hold promise in treatment of certain cardiovascular diseases. See, e.g., Trindade and Rouleau, *Heart Fail. Monit.* 2: 2-7, 2001. However, the measurement of the natriuretic peptides in clinical samples has focused generally upon measurement of BNP, ANP, and/or CNP; their precursor molecules (i.e., pro-BNP, pro-ANP, and pro-CNP); and the fragments resulting from cleavage of the pro-form to provide the mature natriuretic peptides, without consideration of the degradation state of the molecules. It has also been reported that oxidation of methionine residues in the natriuretic peptides reduces the biological activity compared to reduced forms. Koyama et al., *Eur. J. Biochem.* 203: 425-32. For the purposes described herein, the methionine-oxidized forms may be considered products of degradation.

The present invention describes for the first time that assays which have not been designed with an understanding of the degradation pathways of the natriuretic peptides and the products formed during this degradation, may not accurately measure the biologically active forms of a particular natriuretic peptide in a sample. The unintended measurement of both the biologically active natriuretic peptide(s) of interest and inactive fragments derived from the natriuretic peptide may result in an overestimation of the concentration of biologically active natriuretic peptide(s) in a sample. While described hereinafter mainly with reference to BNP-related fragments, the skilled artisan will understand that the general concepts described herein apply equally to ANP- and CNP-related fragments.

The failure to consider the activity of the various natriuretic peptides and their fragments that may be present in a clinical sample when measuring one or more of the natriuretic peptides may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. This inaccuracy may be particularly relevant in the case of severe heart failure, as neutral endopeptidase expression has been reported to be increased in these patients. Knecht et al., *Life Sci.* 71: 2701-12, 2002. This increased expression of the enzyme believed responsible for natriuretic peptide degradation could be expected to increase the inactive fragment pool in these patients.

Overestimation of the natriuretic peptide concentration of a sample may also have serious consequences for patient management. For example, BNP concentration may be used to determine if therapy for congestive heart failure is effective (e.g., by monitoring BNP to see if an elevated level is returning to normal upon treatment). The same "false positive" BNP result discussed above may lead the physician to continue, increase, or modify treatment (e.g., increase the dosage of diuretic, ACE inhibitor, digoxin, (3-blocker, calcium channel blocker, and/or vasodilator, or even consider surgical intervention) because of the false impression that current therapy is ineffective.

Similarly, the present invention describes that assays that have not been designed with an understanding of the glycosylation state of the natriuretic peptides may likewise not accurately measure the forms of a particular natriuretic peptide in a sample. Antibodies are often raised for use in assays through the use of synthetic peptides or expressed peptides that lack the natural glycosylation profile seen in vivo. Consider for example a simple case, where a sandwich immunoassay is provided for BNP, and a significant amount (e.g., 50%) of the BNP present has glycosylation that interferes with antibody binding. An immunoassay formulated with such antibodies will underestimate the amount of BNP present in the sample by 2-fold, potentially resulting in a "false negative" result.

Glycosylation differences amongst the natriuretic peptides may also result in differences in biological activity, either through differences in activity at the natriuretic peptide receptor or through differences in biological half-life due to the glycosylation state of a particular natriuretic peptide. Thus, the methods herein may also be used to generate assays that are specific for certain glycosylation states, again to improve the accuracy of diagnostic and therapeutic utility of such assays.

The skilled artisan will understand that the methods described herein are applicable generally to polypeptides, and the analysis of the natriuretic peptides described in detail herein is merely exemplary. Other suitable polypeptides that may be the subject of similar analysis include angiotensin I, angiotensin II, vasopressin, calcitonin, calcitonin gene related peptide, urodilatin, urotensin II, free cardiac troponin I, free cardiac troponin T, cardiac troponin I in a complex comprising one or both of troponin T and troponin C, cardiac troponin T in a complex comprising one or both of troponin I and troponin C, total cardiac troponin I, total cardiac troponin T, pulmonary surfactant protein D, D-dimer, annexin V, enolase, creatine kinase, glycogen phosphorylase, heart-type fatty acid binding protein, phosphoglyceric acid mutase, S-100, S-100ao, plasmin-α2-antiplasmin complex, β-thromboglobulin, platelet factor 4, fibrinopeptide A, platelet-derived growth factor, prothrombin fragment 1+2, P-selectin, thrombin-antithrombin III complex, von Willebrand factor, tissue factor, thrombus precursor protein, human neutrophil elastase, inducible nitric oxide synthase, lysophosphatidic acid, malondialdehyde-modified low density lipoprotein, matrix metalloproteinase-1, matrix metalloproteinase-2, matrix metalloproteinase-3, matrix metalloproteinase-9, TIMP1, TIMP2, TIMP3, C-reactive protein, interleukin-1β, interleukin-1 receptor antagonist, interleukin-6, tumor necrosis factor α, soluble intercellular adhesion molecule-1, vascular cell adhesion molecule, monocyte chemotactic protein-1, caspase-3, human lipocalin-type prostaglandin D synthase, mast cell tryptase, eosinophil cationic protein, KL-6, procalcitonin, haptoglobin, s-CD40 ligand, S-FAS ligand, alpha 2 actin, basic calponin 1, CSRP2 elastin, LTBP4, smooth muscle myosin, smooth muscle myosin heavy chain, transgelin, aldosterone, angiotensin III, bradykinin, endothelin 1, endotehlin 2, endothelin 3, renin, APO B48, pancreatic elastase 1, pancreatic lipase, sPLA2, trypsinogen activation peptide, alpha enolase, LAMP3, phospholipase D, PLA2G5, protein D, SFTPC, defensin HBD1, defensin HBD2, CXCL-1, CXCL-2, CXCL-3, CCL2, CCL3, CCL4, CCL8, procalcitonin, protein C, serum amyloid A, s-glutathione, s-TNF P55, s-TNF P75, TAFI, TGF beta, MMP-11, brain fatty acid binding protein, CA11, CABP1, CACNA1A, CBLN1, CHN2, cleaved Tau, CRHR1, DRPLA, EGF, GPM6B, GPR7, GPR8, GRIN2C, GRM7, HAPIP, HIF 1 alpha, HIP2 KCNK4, KCNK9, KCNQ5, MAPK10, n-acetyl aspartate, NEUROD2, NRG2, PACE4, phosphoglycerate mutase, PKC gamma, prostaglandin E2, PTEN, PTPRZ1, RGS9, SCAT, secretagogin, SLC1A3, SORL1, SREB3, STAC, STX1A, STXBP1, BDNF, cystatin C, neurokinin A, substance P, interleukin-1, interleukin-11, interleukin-13, interleukin-18, interleukin-4, and interleukin-10.

Glycosylation of Natriuretic Peptides

Glycosylated polypeptides typically comprise N-linked sugars attached to the amino group of one or more asparagine residues; O-linked sugars attached to the hydroxyl group of one or more serine and/or threonine residues; or a combination of N- and O-linked sugars. The present invention demonstrates for the first time that natriuretic peptides are glycosylated. Furthermore, the present invention demonstrates that glycosylation can significantly affect the ability of certain methods of detecting natriuretic peptides in samples.

Several approaches may be used to obviate the potential difficulties presented by glycosylation to a detection scheme. First, one may use chemical or enzymatic treatments to remove carbohydrate residues from the polypeptides, thereby shifting one or more of the naturietic peptides of interest to a "detectable" state if the presence of glycosylation disrupting accurate detection. Second, one may carefully select antibodies that bind to one or more regions of the naturietic peptides of interest that are not subject to interference by glycosylation to provide antibodies that are "insensitive" to a particular glycosylation state. Third, one may carefully select antibodies that bind to one or more regions of the naturietic peptides of interest that are glycosylated, but that exhibit reduced binding in the deglycosylated state, to provide antibodies that are "sensitive" to a particular glycosylation state. Fourth, one may carefully select antibodies that bind to one or more regions of the naturietic peptides of interest that are glycosylated, but that exhibit increased binding in the deglycosylated state, to provide antibodies that are "sensitive" to a particular glycosylation state. One may also combine these approaches as necessary or desired.

Effective enzymatic methods for removing N- and O-linked carbohydrate residues are well known in the art, using enzymes such as N-glycanase (also known as N-glycosidase), endoglycosidase H, endoglycosidase A, O-glycanase (also known as endo-α-N-acetylgalactosaminidase), α2-(3,6,8,9)-neuriminidase, β(1,4)-galactosidase, N-acetylglucosaminidase, endoglycosidase $F_1$, endoglycosidase $F_2$, and/or endoglycosidase $F_3$. This list is not meant to be limiting. Such enzymatic methods of sugar removal from peptides may be used on native (non-denatured) peptides. In such enzymatic methods, however, denaturation of the glycopeptide may be employed, often with an increased rate of deglycosylation. Common denaturation conditions comprise the addition of about 0.01% to about 1% sodium dodecyl sulfate ("SDS"), and optionally about 5 mM to about 500 mM β-mercaptoethanol, in a buffer solution at about neutral pH (i.e., between about pH 6.5 and about pH 8). Such methods may further comprise from about 0.2% to about 2% NP-40, which can serve to stabilize some deglycosylation enzymes. Increased temperature (e.g., about 37° C. for from about 0.5 hours to about 48 hours) may also be employed together with such denaturation conditions.

In the case of non-enzymatic chemical treatments for removal of covalently bound carbohydrate residues from peptides, hydrazine hydrolysis has been found to be effective in the release of unreduced O- and N-linked oligosaccharides. Selective and sequential release of oligosaccharides can be accomplished by initial mild hydrazinolysis of the O-linked oligosaccharides at about 60° C. followed by N-linked oligosaccharides at about 95° C. See, e.g., Patel and Rarekh, *Meth. Enzymol.* 230, 58-66, 1994. Such treatment may result in destruction of the polypeptide however. Alkaline-β-elimination of O-linked oligosaccharides, which utilizes alkaline sodium borohydride in a mild base environment, may be preferred. See, e.g., *Glycobiology: A Practical Approach*, Fukuda, M. and Kobata, A. (Eds), pp. 291-328, IRL/Oxford Univ. Press, Oxford, 1993. In addition, trifluoromethanesulfonic acid hydrolysis may be employed. This method typically leaves an intact polypeptide, but results in destruction of the glycan, as glycosyl linkages between sugars are sensitive to cleavage by trifluoromethanesulfonic acid, but peptide bonds are stable to even prolonged treatment. See, e.g., Edge, *Biochem. J.* 376: 339-50, 2003.

Importantly, changes in mass observed in peptides following such enzymatic or trifluoromethanesulfonic acid treatment can be ascribed to removal of sugar residues, as post-translational modifications other than glycosylation are believed to be stable to such treatments. This can allow for better understanding of the relative contribution of carbohydrates and glycosylation sites to the antigenic epitopes on the polypeptides of interest. Deglycoylation can also allow better understanding of differences in polypeptide mass (e.g., the mass of the natriuretic peptides of interest and fragments thereof present in a sample, which can be related by methods well known to those of skill in the art to the sequence), as the removal of sugar residues removes any doubt as to whether differences in mass observed may be due to differences in sugar content rather than amino acid content.

Selection of Antibodies

The generation and selection of antibodies that preferentially recognize intact natriuretic peptides fragments and/or are sensitive or insensitive to glycosylation state may be accomplished several ways. For example, one way is to purify fragments or to synthesize the fragments of interest using, e.g., solid phase peptide synthesis methods well known in the art. See, e.g., *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990;

Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified intact natriuretic peptide of interest and, if required, comparing the results to the affinity and specificity of the antibodies with natriuretic fragments that are desired to be excluded from binding. The screening procedure can involve immobilization of the purified natriuretic fragments in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized natriuretic peptide(s) and fragments) are present. A similar approach may be used to screen glycosylation-insensitive antibodies. In this case, screening may take place using purified natriuretic fragments containing and lacking one or more carbohydrate residues.

The antibodies so identified may then be further analyzed for affinity and specificity to the natriuretic peptide(s) of interest in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various natriuretic peptides, but these approaches do not change the scope of the invention.

Use of Natriuretic Peptides in Marker Panels

Methods and systems for the identification of one or more markers for the diagnosis, and in particular for the differential diagnosis, of disease have been described previously. Suitable methods for identifying markers useful for the diagnosis of disease states are described in detail in U.S. patent application Ser. No. 10/331,127, entitled Method and System for Disease Detection using Marker Combinations (attorney docket no. 071949-6802), filed Dec. 27, 2002, which is hereby incorporated by reference in its entirety, including all tables, figures, and claims. One skilled in the art will also recognize that univariate analysis of markers can be performed and the data from the univariate analyses of multiple markers can be combined to form panels of markers to differentiate different disease conditions.

In developing a panel of markers useful in diagnosis, data for a number of potential markers may be obtained from a group of subjects by testing for the presence or level of certain markers. The group of subjects is divided into two sets, and preferably the first set and the second set each have an approximately equal number of subjects. The first set includes subjects who have been confirmed as having a disease or, more generally, being in a first condition state. For example, this first set of patients may be those that have recently had a disease incidence, or may be those having a specific type of disease. The confirmation of the condition state may be made through a more rigorous and/or expensive testing such as MRI or CT. Hereinafter, subjects in this first set will be referred to as "diseased".

The second set of subjects is simply those who do not fall within the first set. Subjects in this second set may be "non-diseased;" that is, normal subjects. Alternatively, subjects in this second set may be selected to exhibit one symptom or a constellation of symptoms that mimic those symptoms exhibited by the "diseased" subjects. In still another alternative, this second set may represent those at a different time point from disease incidence.

The data obtained from subjects in these sets includes levels of a plurality of markers, including for purposes of the present invention, one or more fragments of natriuretic peptides either measured individually or as a group. Preferably, data for the same set of markers is available for each patient. This set of markers may include all candidate markers which may be suspected as being relevant to the detection of a particular disease or condition. Actual known relevance is not required. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

A marker often is incapable of definitively identifying a patient as either diseased or non-diseased. For example, if a patient is measured as having a marker level that falls within the overlapping region, the results of the test will be useless in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known to those skilled in the art.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. In a preferred embodiment, the panel response (R) for a each subject (j) is expressed as:

$$R_j = \Sigma w_i I_{i,j},$$

where i is the marker index, j is the subject index, $w_i$ is the weighting coefficient for marker i, I is the indicator value to which the marker level for marker i is mapped for subject j, and $\tau$ is the summation over all candidate markers i.

One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known to those skilled in the art and include several commonly available minimizing or maximizing functions including the Simplex method and other constrained optimization techniques. It is understood by those skilled in the art that some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

Use of Natriuretic Peptides for Determining a Treatment Regimen

A useful diagnostic or prognostic indicator such as the natriuretic peptides can help clinicians select between alternative therapeutic regimens. For example, patients with elevation in cardiac troponin T or I following an acute coronary syndrome appear to derive specific benefit from an early aggressive strategy that includes potent antiplatelet and antithrombotic therapy, and early revascularization. Hamm et al., *N. Engl. J. Med.* 340: 1623-9 (1999); Morrow et al., *J. Am. Coll. Cardiol.* 36: 1812-7 (2000); Cannon et al., *Am. J. Cardiol.* 82: 731-6 (1998). Additionally, patients with elevation in C-reactive protein following myocardial infarction appear to derive particular benefit from HMG-CoA Reductase Inhibitor therapy. Ridker et al., *Circulation* 98: 839-44 (1998). Among patients with congestive heart failure, pilot studies suggest that ACE inhibitors may reduce BNP levels in a dose dependent manner. Van Veldhuisen et al., *J. Am. Coll. Cardiol.* 32: 1811-8 (1998).

Similarly, "tailoring" diuretic and vasodilator therapy based on the level of the biologically active natriuretic peptides may improve outcomes. See, e.g., Troughton et al., *Lancet* 355: 1126-30 (2000). Finally, in a single pilot study of 16 patients found that randomization to an ACE inhibitor rather than placebo following Q-wave MI was associated with reduced BNP levels over the subsequent 6-month period. Motwani et al., *Lancet* 341: 1109-13 (1993). Because BNP is a counter-regulatory hormone with beneficial cardiac and renal effects, it is likely that a change in BNP concentration reflects improved ventricular function and reduced ventricular wall stress. A recent article demonstrates the correlation of NT pro-BNP and BNP assays (Fischer et al., *Clin. Chem.* 47: 591-594 (2001). It is a further objective of this invention that the concentration of natriuretic peptides, either individually or considered in groups of markers, can be used to guide diuretic and vasodilator therapy to improve patient outcome. Additionally, the measurement of natriuretic peptides, either individually or considered in groups of markers, for use as a prognostic indicator for patients is within the scope of the present invention.

Recent studies in patients hospitalized with congestive heart failure suggest that serial BNP measurements may provide incremental prognositic information as compared to a single measurement; that is, assays can demonstrate an improving prognosis when BNP falls after therapy than when it remains persistently elevated. Cheng et al., *J. Am. Coll. Cardiol.* 37: 386-91 (2001). Thus, serial measurements of natriuretic peptides according to the present invention may increase the prognostic and/or diagnostic value of a marker in patients, and is thus within the scope of the present invention.

Assay Measurement Strategies

Numerous methods and devices are well known to the skilled artisan for the detection and analysis of polypeptides or proteins in test samples. In preferred embodiments, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman Access, Abbott AxSym, Roche ElecSys, Dade Behring Stratus systems are among the immunoassay analyzers that are capable of performing the immunoassays taught herein. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the one or more polypeptides is also contemplated by the present invention. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as 'a colored spot.

The analysis of a plurality of polypeptides may be carried out separately or simultaneously with one test sample. For separate or sequential assay, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of polypeptides on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., one or more polypeptides of the invention) for detection at each location. Surfaces may alternatively comprise one or more discrete particles (e.g., microparticles or nanoparticles) immobilized at discrete locations of a surface, where the microparticles comprise antibodies to immobilize one analyte (e.g., one or more polypeptides of the invention) for detection.

In addition, one skilled in the art would recognize the value of testing multiple samples (for example, at successive time points) from the same individual. Such testing of serial samples will allow the identification of changes in polypeptide levels over time. Increases or decreases in polypeptide levels, as well as the absence of change in such levels, would provide useful information about the disease status that includes, but is not limited to identifying the approximate time from onset of the event, the presence and amount of salvagable tissue, the appropriateness of drug therapies, the effectiveness of various therapies as indicated by reperfusion or resolution of symptoms, differentiation of the various types of disease having similar symptoms, identification of the severity of the event, identification of the disease severity, and identification of the patient's outcome, including risk of future events.

A panel consisting of the polypeptides referenced above, and optionally including other protein markers useful in diagnosis, prognosis, or differentiation of disease, may be constructed to provide relevant information related to differential diagnosis. Such a panel may be constructed to detect 1, 2, 3, 4, 5, 6, 7, 8, 9, 10, 15, 20, or more or individual analytes, including one or more polypeptides of the present invention. The analysis of a single analyte or subsets of analytes could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single analyte or a subset of analytes in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W.B. Saunders and Company, p. 496).

The analysis of analytes could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

As discussed above, samples may continue to degrade the natriuretic peptides or fragments thereof, even once the sample is obtained. Thus, it may be advantageous to add one or more protease inhibitors to samples prior to assay. Numerous protease inhibitors are known to those of skill in the art, and exemplary inhibitors may be found in, e.g., The Complete Guide for Protease Inhibition, Roche Molecular Biochemicals, updated Jun. 3, 1999 at roche-applied-science.com/fst/products.htm?/prod_inf/manuals/protease/ prot_toc.htm, and European Patent Application 03013792.1 (published as EP 1 378 242 A1) each of which is hereby incorporated in its entirety. Because various metalloproteases and calcium-dependent proteases are known to exist in blood-derived samples, chelators such as EGTA and/or EDTA, also act as protease inhibitors. In addition, or in the alternative, inhibitors of neutral endopeptidase and/or DPPs may be used.

Inhibition of Natriuretic Peptide Degradation by Prolyl-Specific DPPs

The neurohumoral regulatory system of which natriuretic peptides are a part represents a complex system of cardiovascular regulation. Diseases such as congestive heart failure are, in essence, fatal diseases for which life may be prolonged, but the underlying disease never cured. Thus, there remains a need for novel therapeutic approaches to the management of the underlying diseases, and multiple points in this complex system are seen as important targets by clinicians. The clinical success of angiotensin converting enzyme ("ACE") inhibitors in disease management has led to a search for additional approaches that indirectly affect the course of cardiovascular disease by affecting enzymes that act on vasoactive hormones.

In the case of the natriuretic hormones, increasing hormone levels have been found to have therapeutic potential in patients. See, e.g., Tsekoura et al., *Hellenic J. Cardiol.* 44: 266-70, 2003. Neutral endopeptidase ("NEP") is believed to be a key degradation mediator. Not surprisingly, inhibitors of NEP have found use in treating patients with diseases such as hypertension, atherosclerosis, and heart failure. See, e.g., Corti et al., *Circulation* 104: 1856-62, 2001. Combination treatment with both BNP and NEP inhibitors has been reported to produce a synergistic effect on cardiac output, reduced vascular resistance, and unloading of the heart. Chen et al., *Circulation* 105: 999-1003, 2002. Targeting NEP may suffer from the limitation, however, that NEP metabolizes a broad range of biologically active peptides. See, e.g., Walter et al., *Curr. Opin. Nephrol. Hypertens.* 6: 468-73, 1997.

The present invention describes a novel approach to treatment of cardiovascular disease, particularly heart failure. Several natriuretic peptides, including human forms of pro-BNP, mature BNP, and pro-ANP comprise a penultimate proline residue, rendering the peptides suitable substrates for prolyl-specific dipeptidyl dipeptidases ("DPPs") Inhibitors of DPP have been described as having utility in the management of diabetes, mediated by the inhibition of glucose-dependent insulinotropic polypeptide degradation by DPP IV. See, e.g., Gault et al., *Biochem. Biophys. Res. Commun.* 22: 207-13, 2003. However, their use in treatment of cardiovascular disease has not previously been reported.

Methods for preparing and identifying selective DPP inhibitors are well known in the art. DPP inhibitors include the dipeptide analogues Xaa-boroPro, including Pro-boro-Pro, Ala-boroPro, Val-boroPro, and Lys-boroPro, and dab-pip. See, e.g., Senten et al., *Bioorg. Med. Chem. Lett.* 12: 2825-28, 2002; Jones et al., Blood, prepublished online May 8, 2003; DOI 10.1182. Combinatorial chemistry methods have been used to rapidly synthesize and screen numerous additional dipeptide analogue inhibitors of DPP. See, e.g., Leiting et al., *Biochem. J.* 371: 525-32, 2003; Sedo et al., *Physiol. Res.* 52: 367-72, 2003; Villhauer et al., *J. Med. Chem.* 46: 2774-89, 2003; Senten et al., *J. Comb, Chem.* 5: 336-44, 2003; and U.S. Pat. Nos. 5,602,102; 6,573,287, 6,548,481, 6,432,969, and 6,355,614. The compounds described in these publications may be used as lead compounds in identifying additional DPP inhibitors for use in the methods described herein. A variety of techniques are available in the art for generating combinatorial libraries of small organic molecules. See generally Blondelle et al. *Trends Anal. Chem.* 14: 83, 1995; U.S. Pat. Nos. 5,359,115, 5,362, 899, 5,288,514, and 5,721,099; Chen et al. JACS 116: 2661, 1994; Kerr et al. JACS 115: 252, 1993; WO92/10092, WO93/09668, WO 94/08051, WO93/20242 and WO91/07087. A variety of libraries on the order of about 16 to 1,000,000 or more diversomers can be synthesized and screened for a particular activity or property using the methods described therein.

Preferably, the inhibitors finding use in the invention are small molecules, meaning having a molecular weight of less than about 1000 Daltons. Such inhibitors are well known in the art. See, e.g., WO04/07468 and WO04/50022, and U.S. Pat. Nos. 6,710,040; 6,699,871; 6,432,969; 6,303,661; 6,166,063; 6,124,305; 6,110,949; and 6,107,317, each of which is hereby incorporated by reference in its entirety. Preferred small molecule inhibitors are orally effective. DPP-inhibitory antibody or antibody fragments may also find use in the methods described herein. In this case, antibodies may be generated to DPP and screened (e.g., using the phage display methods described herein) to identify antibodies that inhibit DPP activity on one or more natriuretic peptides of interest.

Compounds may be screened for inhibitory activity using isolated DPP enzymes, cell extracts, or blood derived samples as a source of enzyme, and isolated natriuretic peptides as substrates. Selection of the conditions to inhibit loss of the penultimate proline residue from a target natriuretic peptide may depend on the type of aqueous medium under consideration (for example, inhibition in a blood sample may require conditions that differ from inhibition in the circulation of an organism). Selecting such conditions are within the skill of the artisan. The ability of test compounds and their corresponding pharmaceutically acceptable acid addition salts to inhibit DPP may also be demonstrated by employing a modified version of the assay described in Kubota et al., *Clin. Exp. Immunol.* 89: 192-7, 1992. Confirmation of the presence or absence of the penultimate proline residue may be performed using an immunoassay selected to be sensitive to the loss of this N-terminal portion of the molecule, or through the use of mass spectrometry.

Proceeding to the next step, candidate compounds that modulate DPP activity in cultured cells can be tested in animal models that are relevant to the disease condition of interest. In these methods, labeled natriuretic peptide may be injected into a test animal, and the $T_{1/2}$ for clearance of the natriuretic peptide from the circulation may be determined in the presence and absence of the inhibitor. Preferred animal models of DPP-dependent natriuretic peptide degradation include rats, mice, sheep, dogs, cats, and pigs.

As discussed above, combination treatment with DPP inhibitors and NEP inhibitors and/or natriuretic peptide(s) is contemplated by the invention. In addition or as an alternative, a natriuretic peptide may be provided as an analogue that has been stabilized to DPP activity, as described for glucose-dependent insulinotropic polypeptide in Gault et al., *Metabolism* 52: 679-87, 2003. In preferred embodiments, libraries of natriuretic peptide analogs having one or more substituted, deleted, added, or modified amino acids may be screened for improved stability to DPP degradation. Such analogs preferably retain 50% or more of the natriuretic activity of the parent natriuretic peptide.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. The pharmaceutical compositions also may contain, optionally, suitable preservatives, such as: benzalkonium chloride; chlorobutanol; parabens and thimerosal. Carrier formulation suitable for oral, subcutaneous, intravenous, intramuscular, etc. administrations can be found in Remington's Pharmaceutical Sciences, Mack Publishing Co., Easton, Pa.

A variety of administration routes are available for treating a subject. The particular mode of delivery selected will depend upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, intravenous or parenteral routes. Such modes of administration also include obtaining T cells or bone marrow cells, stem cells or early lineage progenitor cells from a patient and contacting the isolated cells with the compounds of the invention ex vivo, followed by reintroducing the treated cells to the patient. The treated cells can be reintroduced to the patient in any manner known in the art for administering viable cells.

Oral administration is particularly preferred. Compositions suitable for oral administration may be presented as discrete units, such as capsules, tablets, lozenges, each containing a predetermined amount of the compound of the invention. Other compositions include suspensions in aqueous liquids or non-aqueous liquids such as a syrup, elixir or an emulsion. Preferably, the oral preparation does not include an enteric coating since it is desirable to expose the cyclic compounds of the invention to the acidic pH conditions of the digestive tract to convert the cyclic molecules to their linear counterparts.

Other delivery systems can include time-release, delayed release or sustained release delivery systems. Such systems can avoid repeated administrations of the compounds described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, as used herein, means that the implant is constructed and arranged to delivery therapeutic levels of the active ingredient for at least 10 days, and preferably 60 days. Long-term sustained release implants are well-known to those of ordinary skill in the art and include some of the release systems described above.

The selected compounds are administered in effective amounts. An effective amount is a dosage of the compound sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. Generally, doses of active compounds will be from about 0.001 mg/kg per day to 1000 mg/kg per day. It is expected that doses range of 0.001 to 100 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

EXAMPLES

The following examples serve to illustrate the present invention. These examples are in no way intended to limit the scope of the invention.

Example 1

Blood Sampling

Blood is preferably collected by venous puncture using a 20 gauge multi-sample needle and evacuated tubes, although fingertip puncture, plantar surface puncture, earlobe puncture, etc., may suffice for small volumes. For whole blood collection, blood specimens are collected by trained study personnel in EDTA-containing blood collection tubes. For serum collection, blood specimens are collected by trained study personnel in thrombin-containing blood collection tubes. Blood is allowed to clot for 5-10 minutes, and serum is separated from insoluble material by centrifugation. For plasma collection, blood specimens are collected by trained study personnel in citrate-containing blood collection tubes and centrifuged for ≥12 minutes. Samples may be kept at 4° C. until use, or frozen at −20° C. or colder for longer term storage. Whole blood is preferably not frozen.

Example 2

Recombinant Antibody Preparation

Immunization of Mice with Antigens and Purification of RNA from Mouse Spleens

Mice are immunized by the following method based on experience of the timing of spleen harvest for optimal recovery of mRNA coding for antibody. Two species of mice are used: Balb/c (Charles River Laboratories, Wilmington, Mass.) and A/J (Jackson Laboratories, Bar Harbor, Me.). Each of ten mice are immunized intraperitoneally with antigen using 50 µg protein in Freund's complete adjuvant on day 0, and day 28. Tests bleeds of mice are obtained through puncture of the retro-orbital sinus. If, by testing the titers, they are deemed high by ELISA using biotinylated antigen immobilized via streptavidin, the mice are boosted with 50 µg of protein on day 70, 71 and 72, with subsequent sacrifice and splenectomy on day 77. If titers of antibody are not deemed satisfactory, mice are boosted with 50 µg antigen on day 56 and a test bleed taken on day 63. If satisfactory titers are obtained, the animals are boosted with 50 µg of antigen on day 98, 99, and 100 and the spleens harvested on day 105. Typically, a test bleed dilution of 1:3200 or more results in a half maximal ELISA response to be considered satisfactory.

The spleens are harvested in a laminar flow hood and transferred to a petri dish, trimming off and discarding fat and connective tissue. Working quickly, spleens are macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension is pulled through an 18 gauge needle until viscous and all cells are lysed, then transferred to a microcentrifuge tube. The petri dish is washed with 100 µl of solution D to recover any remaining spleen, and this is transferred to the tube. The suspension is then pulled through a 22 gauge needle an additional 5-10 times. The sample is divided evenly between two microcentrifuge tubes and the following added in order, with mixing by inversion after each addition: 100 µl 2 M sodium acetate (pH 4.0), 1.0 ml water-saturated phenol (Fisher Scientific, Pittsburgh, Pa.), 200 µl chloroform/isoamyl alcohol 49:1 (Fisher Scientific, Pittsburgh, Pa.). The solution is vortexed for 10 seconds and incubated on ice for 15 min. Following centrifugation at 14,000 rpm for 20 min at 2-8° C., the aqueous phase is transferred to a fresh tube. An equal volume of water saturated phenol/chloroform/isoamyl alcohol (50:49:1) is added, and the tube vortexed for ten seconds. After a 15 min incubation on ice, the sample is centrifuged for 20 min at 2-8° C., and the aqueous phase transferred to a fresh tube and precipitated with an equal volume of isopropanol at −20° C. for a minimum of 30 min. Following centrifugation at 14,000 rpm for 20 min at 4° C., the supernatant is aspirated away, the tubes briefly spun and all traces of liquid removed. The RNA pellets are each dissolved in 300 µl of solution D, combined, and precipitated with an equal volume of isopropanol at −20° C. for a minimum of 30 min. The sample is centrifuged 14,000 rpm for 20 min at 4° C., the supernatant aspirated as before, and the sample rinsed with 100 µl of ice-cold 70% ethanol. The sample is again centrifuged 14,000 rpm for 20 min at 4° C., the 70% ethanol solution aspirated, and the RNA pellet dried in vacuo. The pellet is resuspended in 100 µl of sterile distilled water. The concentration is determined by A260 using an absorbance of 1.0 for a concentration of 40 µg/ml. The RNA is stored at −80° C.

Preparation of Complementary DNA (cDNA)

The total RNA purified as described above is used directly as template for preparation of cDNA. RNA (50 µg) is diluted to 100 µL with sterile water, and 10 µL-130 ng/mL oligo dT$_{12}$ is added. The sample is heated for 10 min at 70° C., then cooled on ice. 40 µL 5× first strand buffer is added (Gibco/BRL, Gaithersburg, Md.), 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample is then incubated at 37° C. for 2 min. 10 µL reverse transcriptase (Superscript™ II, Gibco/BRL, Gaithersburg, Md.) is added and incubation continued at 37° C. for 1 hr. The cDNA products are used directly for polymerase chain reaction (PCR).

Amplification of cDNA by PCR

To amplify substantially all of the H and L chain genes using PCR, primers are chosen that corresponded to substantially all published sequences. Because the nucleotide sequences of the amino terminals of H and L contain considerable diversity, 33 oligonucleotides are synthesized to serve as 5' primers for the H chains, and 29 oligonucleotides are synthesized to serve as 5' primers for the kappa L chains, as described in U.S. 20030104477. The 5' primers are made according to the following criteria. First, the second and fourth amino acids of the L chain and the second amino acid of the heavy chain are conserved. Mismatches that change the amino acid sequence of the antibody are allowed in any other position. Second, a 20 nucleotide sequence complementary to the M13 uracil template is synthesized on the 5' side of each primer. This sequence is different between the H and L chain primers, corresponding to 20 nucleotides on the 3' side of the pelB signal sequence for L chain primers and the alkaline phosphatase signal sequence for H chain primers. The constant region nucleotide sequences require only one 3' primer each to the H chains and the kappa L chains (FIG. 2). Amplification by PCR was performed separately for each pair of 5' and 3' primers. A 50 µL reaction is performed for each primer pair with 50 pmol of 5' primer, 50 pmol of 3' primer, 0.25 µL Taq DNA Polymerase (5 units/µL, Boehringer Mannheim, Indianapolis, Ind.), 3 µL cDNA (described in Example 2), 5 µL 2 mM dNTP's, 5 µL 10×Taq DNA polymerase buffer with MgCl$_2$ (Boehringer Mannheim, Indianapolis, hid.), and H$_2$O to 50 µL Amplification is done using a GeneAmp® 9600 thermal cycler (Perkin Elmer, Foster City, Calif.) with the following program: 94° C. for 1 mM; 30 cycles of 94° C. for 20 sec, 55° C. for 30 sec, and 72° C. for 30 sec; 72° C. for 6 min; 4° C.

The dsDNA products of the PCR process are then subjected to asymmetric PCR using only 3' primer to generate substantially only the anti-sense strand of the target genes. A 100 µL reaction is done for each dsDNA product with 200 pmol of 3' primer, 2 µL of ds-DNA product, 0.5 µL Taq DNA Polymerase, 10 µL 2 mM dNTP's, 10 µL 10×Taq DNA polymerase buffer with MgCl$_2$ (Boehringer Mannheim, Indianapolis, Ind.), and H$_2$O to 100 µL. The same PCR program as that described above is used to amplify the single-stranded (ss)-DNA.

Purification of ss-DNA by High Performance Liquid Chromatography and Kinasing ss-DNA The H chain ss-PCR products and the L chain ss-PCR products are ethanol precipitated by adding 2.5 volumes ethanol and 0.2 volumes 7.5 M ammonium acetate and incubating at −20° C. for at least 30 min. The DNA is pelleted by centrifuging in an Eppendorf centrifuge at 14,000 rpm for 10 mM at 2-8° C. The supernatant is carefully aspirated, and the tubes briefly spun a 2nd time. The last drop of supernatant is removed with a pipet. The DNA is dried in vacuo for 10 min on medium heat. The H chain products are pooled in 210 µL water and the L chain products are pooled separately in 210 µL water. The ss-DNA is purified by high performance liquid chromatography (HPLC) using a Hewlett Packard 1090 HPLC and a Gen-Pak™ FAX anion exchange column (Millipore Corp., Milford, Mass.) at an oven temperature of 60° C. Absorbance is monitored at 260 nm. The ss-DNA eluted from the HPLC is collected in 0.5 min fractions. Fractions containing ss-DNA are ethanol precipitated, pelleted and dried as described above. The dried DNA pellets are pooled in 200 µL, sterile water.

If desired, the ss-DNA is kinased on the 5' end in preparation for mutagenesis. 24 µL, 10× kinase buffer (United States Biochemical, Cleveland, Ohio), 10.4 µL, 10 mM adenosine-5'-triphosphate (Boehringer Mannheim, Indianapolis, Ind.), and 24, polynucleotide kinase (30 units/

µL, United States Biochemical, Cleveland, Ohio) is added to each sample, and the tubes are incubated at 37° C. for 1 hr. The reactions are stopped by incubating the tubes at 70° C. for 10 min. The DNA is purified with one extraction of equilibrated phenol (pH>8.0, United States Biochemical, Cleveland, Ohio)-chloroform-isoamy-1 alcohol (50:49:1) and one extraction with chloroform: isoamyl alcohol (49:1). After the extractions, the DNA is ethanol precipitated and pelleted as described above. The DNA pellets are dried, then dissolved in 50 µL, sterile water. The concentration is determined by measuring the absorbance of an aliquot of the DNA at 260 nm using 33 µg/mL for an absorbance of 1.0. Samples are stored at −20° C.

Antibody Phage Display Vector

The antibody phage display vector for cloning antibodies is derived from an M13 vector supplied by Ixsys, designated 668-4. The vector 668-4 contained the DNA sequences encoding the heavy and light chains of a mouse monoclonal Fab fragment inserted into a vector described by Huse, WO 92/06024. The vector has a Lac promoter, a pelB signal sequence fused to the 5' side of the L chain variable region of the mouse antibody, the entire kappa chain of the mouse antibody, an alkaline phosphatase signal sequence at the 5' end of the H chain variable region of the mouse antibody, the entire variable region and the first constant region of the H chain, and 5 codons of the hinge region of an IgG1 H chain. A decapeptide sequence is at the 3' end of the H chain hinge region and an amber stop codon separates the decapeptide sequence from the pseudo-gene VIII sequence. The amber stop allows expression of H chain fusion proteins with the gene VIII protein in. *E. coli* suppressor strains such as XL1 blue (Stratagene, San Diego, Calif.), but not in nonsuppressor cell strains such as MK30 (Boehringer Mannheim, Indianapolis, Ind.) (see FIG. 3A).

To make the first derivative cloning vector, deletions are made in the variable regions of the H chain and the L chain by oligonucleotide directed mutagenesis of a uracil template (Kunkel, Proc. Natl. Acad. Sci. USA 82:488 (1985); Kunkel, et al., Methods. Enzymol. 154:367 (1987)). These mutations delete the region of each chain from the 5' end of CDR1 to the 3' end of CDR3, and the mutations add a DNA sequence where protein translation would stop (see FIG. 4 for mutagenesis oligonucleotides). This prevents the expression of H or L chain constant regions in clones without an insert, thereby allowing plaques to be screened for the presence of insert. The resulting cloning vector is called BS11.

Many changes are made to BS11 to generate the cloning vector used in the present screening methods. The amber stop codon between the heavy chain and the pseudo gene VIII sequence is removed so that every heavy chain is expressed as a fusion protein with the gene VIII protein. This increases the copy number of the antibodies on the phage relative to BS11. A HindIII restriction enzyme site in the sequence between the 3' end of the L chain and the 5' end of the alkaline phosphatase signal sequence is deleted so antibodies can be subcloned into a pBR322 derivative. The interchain cysteine residues at the carboxyl-terminus of the L and H chains are changed to serine residues. This increases the level of expression of the antibodies and the copy number of the antibodies on the phage without affecting antibody stability. Nonessential DNA sequences on the 5' side of the lac promoter and on the 3' side of the pseudo gene VIII sequence are deleted to reduce the size of the M13 vector and the potential for rearrangement. A transcriptional stop DNA sequence is added to the vector at the L chain cloning site in addition to the translational stop so that phage with only heavy chain proteins on their surface, which might bind nonspecifically in panning, are not made. Finally, DNA sequences for protein tags are added to different vectors to allow enrichment for polyvalent phage by metal chelate chromatography (polyhistidine sequence) or by affinity purification using a decapeptide tag and a magnetic latex having an immobilized antibody that binds the decapeptide tag. The vector BS39 has a polyhistidine sequence at the 3' end of the kappa chain with no tag at the end of the heavy chain, while BS45 has a polyhistidine sequence between the end of the heavy chain constant region and the pseudo-gene VIII sequence, and a decapeptide sequence at the 3' end of the kappa chain constant region.

Preparation of Uracil Templates Used in Generation of Spleen Antibody Phage Libraries 1 mL of *E. coli* CJ236 (BioRAD, Hercules, Calif.) overnight culture is added to 50 ml 2×YT in a 250 mL baffled shake flask. The culture is grown at 37° C. to $OD_{600}$=0.6, inoculated with 10 µl of a 1/100 dilution of vector phage stock and growth continued for 6 hr. Approximately 40 mL of the culture is centrifuged at 12,000 rpm for 15 minutes at 4° C. The supernatant (30 mL) is transferred to a fresh centrifuge tube and incubated at room temperature for 15 minutes after the addition of 15 µl of 10 mg/ml RNAseA (Boehringer Mannheim, Indianapolis, Ind.). The phage are precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubated on ice for 30 min. The sample is centrifuged at 12,000 rpm for 15 min at 2-8° C. The supernatant is carefully discarded, and the tube is briefly spun to remove all traces of supernatant. The pellet is resuspended in 400 µl of high salt buffer (300 mM NaCl, 100 mM Tris pH 8.0, 1 mM EDTA), and transferred to a 1.5 mL tube. The phage stock is extracted repeatedly with an equal volume of equilibrated phenol:chloroform:isoamyl alcohol (50:49:1) until no trace of a white interface is visible, and then extracted with an equal volume of chloroform:isoamyl alcohol (49:1). The DNA is precipitated with 2.5 volumes of ethanol and 1/5 volume 7.5 M ammonium acetate and incubated 30 min at −20° C. The DNA is centrifuged at 14,000 rpm for 10 mM at 4° C., the pellet washed once with cold 70% ethanol, and dried in vacuo. The uracil template DNA is dissolved in 30 µl sterile water and the concentration determined by A260 using an absorbance of 1.0 for a concentration of 40 µg/ml. The template is diluted to 250 ng/µl with sterile water, aliquoted, and stored at −20° C.

Mutagenesis of Uracil Template with ss-DNA and Electroporation into *E. coli* to Generate Antibody Phage Libraries Antibody phage-display libraries are generated by simultaneously introducing single-stranded heavy and light chain genes onto a phage-display vector uracil template. A typical mutagenesis is performed on a 2 µg scale by mixing the following in a 0.2 mL PCR reaction tube: 8 µl of (250 ng/µl) uracil template (examples 5 and 6), 8 µl of 10× annealing buffer (200 mM Tris pH 7.0, 20 mM $MgCl_2$, 500 mM NaCl), 3.33 µl of kinased single-stranded heavy chain insert (100 ng/µl), 3.1 µl of kinased single-stranded light chain insert (100 ng/ml), and sterile water to 80 µl. DNA is annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA is transferred to ice after the program finishes. The extension/ligation is carried out by adding 8 µl of 10× synthesis buffer (5 mM each dNTP, 10 mM ATP, 100 mM Tris pH 7.4, 50 mM $MgCl_2$, 20 mM DTT), 8 µl T4 DNA ligase (1 U/µl, Boehringer Mannheim, Indianapolis, Ind.), 8

μl diluted T7 DNA polymerase (1 U/μl, New England BioLabs, Beverly, Mass.) and incubated at 37° C. for 30 mM. The reaction is stopped with 300 μl of mutagenesis stop buffer (10 mM Tris pH 8.0, 10 mM EDTA). The mutagenesis DNA is extracted once with equilibrated phenol (pH>8): chloroform:isoamyl alcohol (50:49:1), once with chloroform:isoamyl alcohol (49:1), and the DNA is ethanol precipitated at −20° C. for at least 30 min. The DNA is pelleted and the supernatant carefully removed as described above. The sample is briefly spun again and all traces of ethanol removed with a pipetman. The pellet is dried in vacuo. The DNA is resuspended in 4 μl of sterile water.

1 μl mutagenesis DNA is (500 ng) is transferred into 40 μl electrocompetent E. coli DH12S (Gibco/BRL, Gaithersburg, Md.). The transformed cells are mixed with 1.0 mL 2×YT broth and transferred to 15 mL sterile culture tubes. The first round antibody phage is made by shaking the cultures overnight at 23° C. and 300 rpm. The efficiency of the electroporation is measured by plating 10 μl of $10^{-3}$ and $10^{-4}$ dilutions of the cultures on LB agar plates. These plates are incubated overnight at 37° C. The efficiency is determined by multiplying the number of plaques on the $10^{-3}$ dilution plate by $10^5$ or multiplying the number of plaques on the $10^4$ dilution plate by $10^6$. The overnight cultures from the electroporations are transferred to 1.5 ml tubes, and the cells are pelleted by centrifuging at 14,000 rpm for 5 min. The supernatant, which is the first round of antibody phage, is then transferred to 15 mL sterile centrifuge tubes with plug seal caps.

Transformation of E. coli by Electroporation

The electrocompetent E. coli cells are thawed on ice. DNA is mixed with 20-40 μL electrocompetent cells by gently pipetting the cells up and down 2-3 times, being careful not to introduce air-bubbles. The cells are transferred to a Gene Pulser cuvette (0.2 cm gap, BioRAD, Hercules, Calif.) that has been cooled on ice, again being careful not to introduce an air-bubble in the transfer. The cuvette is placed in the E. coli Pulser (BioRAD, Hercules, Calif.) and electroporated with the voltage set at 1.88 kV according to the manufacturer's recommendation. The transformed sample is immediately diluted to 1 ml with 2×YT broth and processed as procedures dictate.

Preparation of Biotinylated Antigens and Antibodies

Protein antigens or antibodies are dialyzed against a minimum of 100 volumes of 20 mM borate, 150 mM NaCl, pH 8 (BBS) at 2-8° C. for at least 4 hr. The buffer is changed at least once prior to biotinylation. Protein antigens or antibodies are reacted with biotin-XX-NHS ester (Molecular Probes, Eugene, Oreg., stock solution at 40 mM in dimethylformamide) at a final concentration of 1 mM for 1 hr at room temperature. After 1 hr, the protein antigens or antibodies are extensively dialyzed into BBS to remove unreacted small molecules.

Preparation of Alkaline Phosphatase-Antigen Conjugates

Alkaline phosphatase (AP, Calzyme Laboratories, San Luis Obispo, Calif.) is placed into dialysis versus a minimum of 100 volumes of column buffer (50 mM potassium phosphate, 10 mM borate, 150 mM NaCl, 1 mM MgSO$_4$, pH 7.0) at 2-8° C. for at least four hr. The buffer is changed at least twice prior to use of the AP. When the AP is removed from dialysis and brought to room temperature, the concentration is determined by absorbance at 280 nm using an absorbance of 0.77 for a 1 mg/mL solution. The AP is diluted to 5 mg/mL with column buffer. The reaction of AP and succinimidyl 4-(N-maleimidomethyl) cyclohexane-1-carboxylate (SMCC, Pierce Chemical Co., Rockford, Ill.) is carried out using a 20:1 ratio of SMCC:AP. SMCC is dissolved in acetonitrile at 20 mg/mL and diluted by a factor of 84 when added to AP while vortexing or rapidly stirring. The solution is allowed to stand at room temperature for 90 min before the unreacted SMCC and low molecular weight reaction products are separated from the AP using gel filtration chromatography (G50 Fine, Pharmacia Biotech, Piscataway, N.J.) in a column equilibrated with column buffer.

Protein antigen is dialyzed versus a minimum of 100 volumes of 20 mM potassium phosphate, 4 mM borate, 150 mM NaCl, pH 7.0 at 2-8° C. for at least four hr. The buffer is changed at least twice prior to use of the antigen. The amount of antigen is quantitated by absorbance at 280 nm or by the method of Lowry. The reaction of antigen and N-succinimidyl 3-[2-pyridyldithio]propionate (SPDP, Pierce Chemical Co., Rockford, Ill.) is carried out using a 20:1 molar ratio of SPDP:antigen. SPDP is dissolved in dimethylformamide at 40 mM and diluted into the antigen solution while vortexing. The solution is allowed to stand at room temperature for 90 min, at which time the reaction is quenched by adding taurine (Aldrich Chemical Co., Milwaukee, Wis.) to a final concentration of 20 mM for 5 min. Dithiothreitol (Fisher Scientific, Pittsburgh, Pa.) is added to the protein at a final concentration of 1 mM for 30 min. The low molecular weight reaction products are separated from the antigen using gel filtration chromatography in a column equilibrated in 50 mM potassium phosphate, 10 mM borate, 150 mM NaCl, 0.1 mM ethylene diamine tetraacetic acid (EDTA, Fisher Scientific, Pittsburgh, Pa.), pH 7.0.

The AP and antigen are mixed together in an equimolar ratio. The reaction is allowed to proceed at room temperature for 2 hr. The conjugate is diluted to 0.1 mg/mL with block containing 1% bovine serum albumin (from 30% BSA, Bayer, Kankakee, Ill.), 10 mM Tris, 150 mM NaCl, 1 mM MgCl$_2$, 0.1 mM ZnCl$_2$, 0.1% polyvinyl alcohol (80% hydrolyzed, Aldrich Chemical Co., Milwaukee, Wis.), pH 8.0.

Preparation of Avidin Magnetic Latex

Magnetic latex (Estapor, 10% solids, Bangs Laboratories, Fishers, Ind.) is thoroughly resuspended and 2 ml aliquoted into a 15 ml conical tube. The magnetic latex is suspended in 12 ml distilled water and separated from the solution for 10 mM using a magnet. While still in the magnet, the liquid is carefully removed with a 10 mL sterile pipet. This washing process is repeated an additional three times. After the final wash, the latex is resuspended in 2 ml of distilled water. In a separate 50 ml conical tube, 10 mg of avidin-HS (NeutrAvidin, Pierce, Rockford, Ill.) is dissolved in 18 ml of 40 mM Tris, 0.15 M sodium chloride, pH 7.5 (TBS). While vortexing, the 2 ml of washed magnetic latex is added to the diluted avidin-HS and the mixture vortexed an additional 30 seconds. This mixture is incubated at 45° C. for 2 hr, shaking every 30 minutes. The avidin magnetic latex is separated from the solution using a magnet and washed three times with 20 ml BBS as described above. After the final wash, the latex is resuspended in 10 ml BBS and stored at 4° C.

Immediately prior to use, the avidin magnetic latex is equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 μl/sample) is added to a sterile 15 ml centrifuge tube and brought to 10 ml with panning buffer. The tube is placed on the magnet for 10 min to separate the latex. The solution is carefully removed with a 10 mL sterile pipet as described above. The magnetic latex is resuspended in 10 mL of panning buffer to begin the second wash. The magnetic latex is washed a total of 3 times with panning buffer. After the final wash, the latex is resuspended in panning buffer to the initial aliquot volume.

Plating M13 Phage or Cells Transformed with Antibody Phage-Display Vector Mutagenesis Reaction The phage samples are added to 200 µL of an overnight culture of *E. coli* XL 1-Blue when plating on 100 mm LB agar plates or to 600 µL of overnight cells when plating on 150 mm plates in sterile 15 ml culture tubes. After adding LB top agar (3 mL for 100 mm plates or 9 mL for 150 mm plates, top agar stored at 55° C., Appendix Al, Molecular Cloning, A Laboratory Manual, (1989) Sambrook. J), the mixture is evenly distributed on an LB agar plate that had been pre-warmed (37° C.-55° C.) to remove any excess moisture on the agar surface. The plates are cooled at room temperature until the top agar solidified. The plates are inverted and incubated at 37° C. as indicated.

Develop Nitrocellulose Filters with Alkaline Phosphatase Conjugates

After overnight incubation of the nitrocellulose filters on LB agar plates, the filters are carefully removed from the plates with membrane forceps and incubated for 2 hr in either casein block (block with 1% casein (Hammersten grade, Research Organics, Cleveland, Ohio)), when using antigen-AP conjugates or block when using goat anti-mouse kappa-AP (Southern Biotechnology Associates, Inc., Birmingham, Ala.). After 2 hr, the filters are incubated with the AP conjugate for 2-4 hr. Antigen-AP conjugates are diluted into casein block at a final concentration of 1 µg/mL and goat anti-mouse kappa-AP conjugates are diluted into block at a final concentration of 1 µg/mL. Filters are washed 3 times with 40 mM TRIS, 150 mM NaCl, 0.05% Tween 20, pH 7.5 (TBST) (Fisher Chemical, Pittsburgh, Pa.) for 5 mM each. After the final wash, the filters are developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

Enrichment of Polyclonal Phage to BNP Peptides with No Tags on the Heavy Chain and a Polyhistidine Sequence on the Kappa Chain This example describes multiple rounds of screening of a phage library to BNP peptides. Some of the rounds of screening are alternated with rounds of enrichment for phage displaying multiple copies of antibodies. The percentage of phage displaying any light chain, and the percentage of phage displaying Fab fragments with specific affinity for BNP peptides of interest (referred to below as "antigen") is measured after each round of screening.

The first round antibody phage is prepared as described above using BS39 uracil template. Two electroporations of mutagenesis DNA had efficiencies of $9.7 \times 10^7$ PFU and $8.3 \times 10^7$ PFU. The phage from both electroporations are combined and diluted to 3.2 ml with panning buffer. The phage is aliquoted into 2-1 mL aliquots in 15 mL disposable sterile centrifuge tubes with plug seal caps. Antigen-biotin (10 µL, $10^{-6}$ M stock concentration) is added to each phage aliquot. The phage samples are incubated overnight at 2-8° C.

After the incubation, the phage samples are panned with avidin magnetic latex. The equilibrated avidin magnetic latex (see Example 11), 200 µL latex per sample, is incubated with the phage for 10 min at room temperature. After 10 min, approximately 9 mL of panning buffer is added to each phage sample, and the magnetic latex is separated from the solution using a magnet. After 10 min in the magnet, the unbound phage is carefully removed with a 10 mL sterile pipet. The magnetic latex is then resuspended in 10 mL of panning buffer to begin the second wash. The latex is washed a total of 5 times as described above. For each wash, the tubes are in the magnet for 10 min to separate unbound phage from the magnetic latex. After the 5th wash, the magnetic latex is resuspended in 1 mL TBS and transferred to a 1.5 mL tube. Aliquots of the latex are taken at this point to plate on 100 mm LB agar plates as described above. The bulk of the magnetic latex (99%) is resuspended in 200 µL 2×YT and is plated on a 150 mm LB agar plate as described in Example 12. The 100 mm LB agar plates are incubated at 37° C. for 6-7 hr, then the plates are transferred to room temperature and nitrocellulose filters (pore size 0.45 µm, BA85 Protran, Schleicher and Schuell, Keene, N.H.) are overlayed onto the plaques. Plates with nitrocellulose filters are incubated overnight at room temperature. The 150 mm plates are used to amplify the phage binding to the magnetic latex to generate the next round of antibody phage. These plates are incubated at 37° C. for 4 hr, then overnight at 20° C.

After the overnight incubation, the antibody phage is eluted from the 150 mm plates, and the filters are developed with alkaline phosphatase-antigen as described herein. The antibody phage is eluted from the 150 mm plates by pipetting 8 mL 2YT media onto the lawn and gently shaking the plate at room temperature for 20 min. The phage are transferred to a 15 mL disposable sterile centrifuge tubes with plug seal cap and the debris from the LB plate is pelleted by centrifuging for 15 min at 3500 rpm. The 2nd round antibody phage is then transferred to a new tube.

To begin the 2nd round of panning, the antibody phage are titered by plating 10 µL of $10^{-7}$ and $10^{-8}$ dilutions of the phage on 100 mm LB agar plates. The plates are incubated at 37° C. for 6-7 hr, then the number of plaques on the plates are counted. Also, to monitor the percentage of kappa positives in the antibody phage, a nitrocellulose filter is overlayed onto the plate and incubated overnight at room temperature. The percentage of kappa positives is a measure of the proportion of phage displaying intact Fab fragments.

Both 2nd round antibody phage samples are pooled by diluting each sample into panning buffer at a final concentration of $5 \times 10^9$ PFU/mL to a final volume of 1 mL. (The titers of the antibody phage are about $2 \times 10^{12}$ PFU/mL and $1.7 \times 10^{12}$). Antigen-biotin (10 µL, $10^{-6}$ M stock concentration) is added to the phage and the phage is incubated at 2-8° C. overnight. The nitrocellulose filters on the antibody phage titer plates are developed with goat anti-mouse kappa AP as described herein. The second round antibody phage is panned with avidin magnetic latex as described above. After washing the latex with panning buffer, the latex is resuspended in 1 mL TBS and transferred to a 1.5 mL tube. Aliquots of the latex are plated on 100 mm LB agar plates as described above to check functional positives, and the rest of the latex is plated on 150 mm LB agar plates to generate the 3rd round antibody phage. This general procedure of titering the antibody phage, diluting the phage into panning buffer and adding antigen-biotin, incubating the phage at least 16 hr at 2-8° C., panning the phage with avidin magnetic latex, and plating the magnetic latex is followed through 10 rounds of panning. The only changes from that described above is the concentration of antigen-biotin is lower to increase the affinity of bound antibodies, and the number of phage panned is between $10^{10}$ and $10^8$.

After the 10th round of panning to antigen-biotin, the antibody phage are subject to a round of enrichment for polyvalent display. Enrichment is effected by binding of the hexahistidine tag fused to the displayed light chain to Ni NTA agarose (Qiagen Inc., Chatsworth, Calif.). The 11th round antibody phage (2.5 mL) are diluted into 2.5 mL panning buffer in a 15 mL disposable sterile centrifuge tube with plug seal cap. The Ni NTA is equilibrated into panning buffer using the following procedure. The resin (1 mL per phage sample) is diluted to 50 mL with panning buffer in a 50 mL disposable sterile centrifuge tube with plug seal cap and then is pelleted in an IEC centrifuge at 500 rpm for 1 min. The supernatant is carefully removed with a 50 mL disposable pipet, and the resin is again diluted to 50 mL with panning buffer for the second wash. The resin is washed in this manner a total of 4 times in order to equilibrate the resin in panning buffer. The equilibrated resin is then resuspended to its original volume with panning buffer. Equilibrated resin (1 mL) is then added to the phage, and the tube is gently rocked for 15 min. After 15 min, the resin is pelleted in an IEC centrifuge at 500 rpm for 1 min. The supernatant is gently removed with a 10 mL disposable pipet, and the resin is resuspended in 10 mL panning buffer for the first wash. The resin is pelleted as described above, the supernatant is removed, and the resin is resuspended a 2nd time in 10 mL panning buffer. This procedure is repeated for a total of 5 panning buffer washes. After the 5th wash is removed, the resin is resuspended in 1 mL of elution buffer (50 mM citrate, 150 mM NaCl, pH 4.0) and transferred to a 1.5 mL tube. The resin is gently rocked for 1 hr to elute the antibody phage. After 1 hr, the resin is pelleted (14,000 rpm in Eppendorf centrifuge for 5 min), and the phage is removed while being careful not to transfer any resin. In order to adjust the pH of the phage solution to 8, 50 µL of 1 M Tris, pH 8.3 and 46 µL of 1 M NaOH are added to the 1 mL phage sample. Also, 10 1 L of 300 mg/mL bovine serum albumin (Bayer, Kankakee, Ill.) is added to the phage sample. The resulting phage solution (1 mL) is transferred to a 15 mL disposable sterile centrifuge tube with plug seal cap for the 11th round of panning with antigen-biotin, as described above.

The 12th-14th rounds of panning are done as described above, where the antibody phage is bound to Ni NTA, eluted, and the eluted phage panned with antigen-biotin. However, in round 13, unlabeled C-terminal BNP peptides are added to the phage eluted from the Ni NTA at 100-fold molar excess to the antigen-biotin to select antibodies that specifically bind to antigen without binding to the C-terminal BNP peptides.

Example 3

Biochemical Analyses

BNP is measured using standard immunoassay techniques. These techniques involve the use of antibodies to specifically bind the protein targets. An antibody directed against BNP is biotinylated using N-hydroxysuccinimide biotin (NHS-biotin) at a ratio of about 5 NHS-biotin moieties per antibody. The biotinylated antibody is then added to wells of a standard avidin 384 well microtiter plate, and biotinylated antibody not bound to the plate is removed. This formed an anti-BNP solid phase in the microtiter plate. Another anti-BNP antibody is conjugated to alkaline phosphatase using standard techniques, using SMCC and SPDP (Pierce, Rockford, Ill.). The immunoassays are performed on a TECAN Genesis RSP 200/8 Workstation. Test samples (10 µL) are pipeted into the microtiter plate wells, and incubated for 60 min. The sample is then removed and the wells washed with a wash buffer, consisting of 20 mM borate (pH 7.42) containing 150 mM NaCl, 0.1% sodium azide, and 0.02% Tween-20. The alkaline phosphatase-antibody conjugate is then added to the wells and incubated for an additional 60 min, after which time, the antibody conjugate is removed and the wells washed with a wash buffer. A substrate, (AttoPhos®, Promega, Madison, Wis.) is added to the wells, and the rate of formation of the fluorescent product is related to the concentration of the BNP in the test samples.

Example 4

Synthesis of DPP Inhibitors

Peptide coupling chemistry is preferably employed to prepare linear boroPro compounds. The peptide coupling chemistry methods and procedures used in this invention are readily available. Examples of books using these methods include, but are not limited to, the following citations incorporated herein by reference: P. D. Bailey, "An Introduction to Peptide Chemistry," John Wiley & Sons, 1990; Miklos Bodansky, "Peptide Chemistry A Practical Textbook," Springer-Verlag, 1988; Miklos Bodansky, "Principles of Peptide Synthesis, Reactivity and Structure Concepts in Organic Chemistry," Volume 16, Springer-Verlag, 1984; and Miklos Bodansky, "Principles of Peptide Synthesis, Reactivity and Structure Concepts in Organic Chemistry," Volume 21, Springer-Verlag, 1984.

The compounds of the invention can begin with the synthesis of H-boroPro as disclosed in WO 98/00439. Use of H-boroPro is for illustrative purposes only, and is not intended to limit the scope of this invention. According to WO 98/00439, H-boroPro may be prepared by the synthetic route previously developed and described (G. R. Flentke, et al., "Inhibition of dipeptidyl aminopeptidase IV (DP-IV) by Xaa-boroPro dipeptides and use of these inhibitors to examine the role of DP-IV in T-cell function," PNAS (U.S.A.) 88, 1556-1559 (1991); also described in U.S. Pat. No. 5,462,928). Alternatively, H-boroPro may be produced by a new procedure (Kelly, T. A., et al., "The efficient synthesis and simple resolution of a proline boronate ester suitable for enzyme inhibition studies," Tetrahedron 49, 1009-1016 (1993)). Both of these synthetic routes reportedly yield racemic H-boroPro pinanediol.

According to WO 98/00439, stereochemically pure L, L and L, D diastereomers of Z-Lys-boroPro are prepared by first resolving racemic H-boroPro through crystallization with optically active blocking protecting groups ((1S, 2S, 3R, 5S)-+-pinanediol isomer) followed by coupling the isotopically pure L-boroPro and D-boroPro to the stereochemically pure L isomer of lysine (See U.S. Pat. No. 5,462,928). Alternatively, the L,L and L,D diastereomers of Lys-boroPro are prepared in high optical purity by coupling racemic H-boroPro by L-Lys and separating the resulting diastereomeric Z-Lys-boroPro-diester into its component L,D and L,L diastereomers using reverse phase HPLC as previously described for diastereomeric Pro-boroPro (W. G. Gutheil and W. W. Bachovchin, "Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition," Biochemistry 32, 8723-8731 (1993)).

Example 5

Purification of Dipeptidyl Peptidase

The following examples are exemplary for dipeptidyl peptidase IV; dipeptidyl peptidase II may be isolated and used similarly according to the methods of U.S. Pat. No. 6,485,955.

Porcine enzyme is purified as previously described (1), with several modifications. Kidneys from 15-20 animals are obtained, and the cortex dissected away and frozen at −80° C. Frozen tissue (2000-2500 g) is homogenized in 12 L of 0.25 M sucrose in a Waring blender. The homogenate is left at 37° C. for 18 hours to facilitate cleavage of DPP4 from cell membranes. After the cleavage step, the homogenate is clarified by centrifugation at 7000×g for 20 minutes at 4° C., and the supernatant is collected. Solid ammonium sulfate is added to 60% saturation, and the precipitate is collected by centrifugation at 10,000×g and discarded. Additional ammonium sulfate is added to the supernatant to 80% saturation, and the 80% pellet is collected and dissolved in 20 mM $Na_2HPO_4$, pH 7.4.

After dialysis against 20 mM $Na_2HPO_4$, pH 7.4, the preparation is clarified by centrifugation at 10,000×g. The clarified preparation then is applied to 300 ml of ConA Sepharose equilibrated in the same buffer. After washing with buffer to a constant A280, the column is eluted with 5% (wt/vol) methyl α-D-mannopyranoside. Active fractions are pooled, concentrated, and dialyzed against 5 mM sodium acetate, pH 5.0. Dialyzed material is flowed through a 100 ml Pharmacia Resource S column equilibrated in the same buffer. The flowthrough material is collected and contained most of the enzyme activity. Active material again is concentrated and dialyzed into 20 mM $Na_2HPO_4$, pH 7.4. Lastly, the concentrated enzyme is chromatographed on a Pharmacia S-200 gel filtration column to removed low molecular weight contaminants. Purity of column fractions is analyzed by reducing SDS-PAGE, and the purest fractions pooled and concentrated. Purified enzyme is stored in 20% glycerol at −80° C.

Example 6

Assay of Dipeptidyl Peptidase

Enzyme is assayed under steady-state conditions as previously described in Nagatsu et al., *Anal. Biochem.* 74: 466-76, 1976 with BNP as substrate, with the following modifications. Reactions contain, in a final volume of 100 μL, 100 mM ACES, 52 mM TRIS, 52 mM ethanolamine, 500 μM substrate, 0.2% DMSO, and 4.5 nM enzyme at 25° C., pH 7.4. For analysis of positive compounds, steady-state kinetic inhibition constants are determined as a function of both substrate and inhibitor concentration. Complete inhibition experiments contain 11 substrate and 7 inhibitor concentrations, with triplicate determinations. For tight binding inhibitors with K, s less than 20 nM, the enzyme concentration is reduced to 0.5 nM and reaction times are increased to 120 minutes. Pooled datasets from the three plates are fitted to the appropriate equation for either competitive, noncompetitive or uncompetitive inhibition.

Example 7

Chemical Deglycosylation of Naturietic Peptides

50 μg of protein is incubated at 4° C. for 2 hours in the dark, with 100 μl of trifluoromethanesulfonic acid/anisole (2:1, v/v) reagent in glass tubing saturated with $N_2$. The reaction is stopped by the addition of 60% (v/v) pyridine at −20° C. The protein is extensively dialysed against 25 mM sodium phosphate buffer pH 7.0.

Example 8

Enzymatic Deglycosylation of Naturietic Peptides

To 40 μL of sample is added 2 μL 25× protease inhibitor cocktail (Sigma cat. # P2714), 1 μL O-glycanase (Prozyme cat. # GK80090), 3 μL sialidase A (Prozyme cat. # GK80040), and 8 μL 200 mM sodium phosphate buffer pH 7.0. The mixture is vortexed gently and incubated at 20° C. for 4 hours.

Example 9

Analysis of Natriuretic Peptides by Mass Spectrometry

Preparation of Antibody Capture Surface

3 μL of antibody solution (0.25 mg/mL anti-BNP monoclonal antibody in borate buffered saline pH 8.0 ("BBS")) is applied to appropriate spots of a PS10 ProteinChip array (Ciphergen cat. # C553-0044), and the chip is placed in a humid chamber with gentle agitation at 20° C. for 3 hours. The antibody solution is removed, and the array spots are washed twice with 3 μL of 1.5 mg/mL BSA/0.1% Triton X-100/0.5 M Tris-HCl pH 8.0. At the second wash, the chip is placed in a humid chamber without agitation at 20° C. for 3 hours. Following this wash, the array is immersed in 5 mM HEPES pH 7.5, and the excess buffer is removed.

Capture of BNP

Using a BIOMEC robotic pipetting station (Beckman Instruments), the array is washed with 150 μL, 1% Triton X-100 in BBS for 10 minutes; 150 μL, 10% PEG300/0.1% Triton X-100 in BBS for 10 minutes; and 3× with 150 μL, 0.2% Triton X-100 in BBS for 5 minutes each. 40 μL 0.2% Triton X-100 in BBS and 40 μL deglycosylated sample (or control sample) is applied and incubated overnight at 4° C. with gentle agitation.

Application of Energy Absorbing Matrix and MS Analysis

Following this incubation, the array is washed 3× with 150 μL 1M urea/0.1% CHAPS/0.3M KCl/50 mM Tris-HCl pH 7.5 for 1 minute each; and 3× with 300 μL 5 mM HEPES pH 7.5 for 3 seconds each. Excess buffer is removed, and the array is allowed to air dry until no sheen is visible. For low molecular weight analysis (M/Z<6000), 1 μL of 20% α-cyano-4-hydroxycinnamic acid (CHCA, Ciphergen cat. # C300-0001) in 0.5% trifluoroacetic acid (Pierce cat #28904)/50% acetonitrile (Pierce cat. #20062) is applied to appropriate spots as an energy absorbing matrix ("EAM"). For high molecular weight analysis (M/Z>6000), 1 μL of 50% sinapinic acid (SPA, Ciphergen Cat. No. C300-0002) in 0.5% trifluoroacetic acid/50% acetonitrile is applied to appropriate spots as an EAM. Spots are allowed to air dry, and a second 1 μL drop of the appropriate EAM is applied.

MS spectra are acquired using a Ciphergen ProteinChip reader model PBS IIC. For low molecular weight analysis, the following instrument parameters are used: high mass is set to 70 kDa optimized from 2 kDa to 15 kDa; starting laser intensity is set to 165; starting detector sensitivity is set to 9; mass deflector is set to 1 kDa; acquisition method is set to SELDI quantitation; SELDI acquisition parameters=26, delta=10, transients per=18, ending position=76; and warming positions with 5 shots at intensity=175. For high molecular weight analysis, the following instrument parameters are used: high mass is set to 70 kDa optimized from 3 kDa to 30 kDa; starting laser intensity is set to 200; starting detector sensitivity is set to 9; mass deflector is set to 2 kDa;

acquisition method is set to SELDI quantitation; SELDI acquisition parameters=24, delta=10, transients per=13, ending position=74; and warming positions with 3 shots at intensity=210.

Example 10

Inhibition of BNP Degradation

Two human plasma samples were individually divided into two tubes, to one of which the reversible DPP inhibitor Diprotin A (Ile-Pro-Ile) was added to a concentration of 1 mM. Each sample was spiked with human $BNP_{77-108}$, and the mixture held at 4° C. overnight. Each sample was subjected to antibody capture SELDI mass spectrometry as described above. The results are depicted in FIG. 1. Panels A (no addition) and B (Diprotin A) represent one plasma sample, and panels C (no addition) and D (Diprotin A) the second plasma sample. Capture was performed with an antibody that recognizes human BNP.

Full length $BNP_{77-108}$ would be expected to appear at a molecular weight of about 3466 Da (large arrowhead), and $BNP_{79-1138}$ (in which cleavage occurs following the penultimate proline) at about 3282 Da (small arrowhead). Comparing panels A to B and C to D, the cleavage of $BNP_{77-108}$ to $BNP_{79-408}$ is inhibited by the DPP inhibitor. A second cleavage product, presumed to be $BNP_{79-106}$ at a molecular weight of about 2988 Da, is also inhibited by the Diprotin A treatment, with a corresponding increase in a cleavage product presumed to be $BNP_{77-106}$ at a molecular weight of about 3173 Da. Thus, removal of the amino terminal ser-pro dipeptide is sensitive to the presence of a DPP inhibitor, while a second carboxyl terminal dipeptide cleavage is not.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

I claim:

1. An improved immunoassay method for determining the presence or amount of a biologically active natriuretic peptide of interest, comprising;
   contacting a sample with a first antibody selected to bind biologically active forms of the natriuretic peptide of interest;
   contacting the sample with a second antibody selected to bind all biologically active and biologically inactive forms of the natriuretic peptide of interest;
   contacting the sample with a third antibody selected to bind the biologically active and biologically inactive forms of the natriuretic peptide when complexed with the first or second antibodies respectively; and
   determining a first assay signal due to the first antibody and a second assay signal due to the second antibody present in complex with the third antibody;
   wherein the first assay signal represents the amount of biologically active natriuretic peptide of interest and the second signal represents the total amount natriuretic peptide of interest in the sample.

2. The method of claim 1, wherein the biologically active natriuretic peptide of interest is lacking a N-terminal region.

3. The method of claim 1, wherein the biologically active natriuretic peptide of interest is glycosylated.

4. The method of claim 1, wherein one or more antibodies are selected such that in the immunoassay, the one or more antibodies detect a biologically active form of the natriuretic peptide of interest and exhibits a signal at least a factor of 5 greater than the signal exhibited from detection of a biologically inactive form of the natriuretic peptide of interest.

5. The method of claim 1, wherein one or more antibodies are selected such that in the immunoassay the one or more antibodies bind to one or more regions of the natriuretic peptides of interest that are not subject to interference by glycosylation.

6. The method of claim 1, wherein one or more antibodies are selected such that in the immunoassay the one or more antibodies bind to one or more regions of the natriuretic peptides of interest that are glycosylated, but that exhibit reduced binding in the nonglycosylated state.

7. The method of claim 1, wherein one or more antibodies are selected such that in the immunoassay the one or more antibodies bind to one or more regions of the natriuretic peptides of interest that are glycosylated, but that exhibit increased binding in the nonglycosylated state.

8. The method of claim 1, wherein the first, second or third antibodies are each conjugated to a detectable label.

9. The method of claim 8, wherein the label is a fluorescent or luminescent tag, a metal, a dye, a radionuclide, or an enzyme.

10. The method of claim 1, wherein the first, second or third antibodies are immobilized onto a solid support.

11. The method of claim 10, wherein the solid support is a magnetic particle, a chromatographic matrix particle, the surface of an assay plate, a piece of solid substrate material, or a piece of membrane.

* * * * *